US012285499B2

(12) United States Patent
Timm et al.

(10) Patent No.: US 12,285,499 B2
(45) Date of Patent: *Apr. 29, 2025

(54) TISSUE STAIN AND USE THEREOF

(71) Applicant: GI SUPPLY, Mechanicsburg, PA (US)

(72) Inventors: Mary Jo Timm, Littleton, MA (US); Robert G. Whalen, Willington, CT (US); Amy A. Cameron, Union, CT (US); Patrick Lee, Long Grove, IL (US)

(73) Assignee: GI SUPPLY, Mechanicsburg, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/942,390

(22) Filed: Sep. 12, 2022

(65) Prior Publication Data

US 2023/0001022 A1  Jan. 5, 2023

Related U.S. Application Data

(63) Continuation of application No. 15/690,178, filed on Aug. 29, 2017, now Pat. No. 11,452,783.

(51) Int. Cl.
*A61K 49/00* (2006.01)
*A61B 90/00* (2016.01)

(52) U.S. Cl.
CPC ........ *A61K 49/006* (2013.01); *A61K 49/0093* (2013.01); *A61B 90/39* (2016.02); *A61B 2090/395* (2016.02)

(58) Field of Classification Search
CPC .. A61K 49/006; A61K 49/0093; A61B 90/39; A61B 2090/395; G01N 1/30; G01N 2001/302

See application file for complete search history.

(56) References Cited

U.S. PATENT DOCUMENTS

| | | | |
|---|---|---|---|
| 5,122,147 A | 6/1992 | Sewell, Jr. | |
| 5,328,504 A | 7/1994 | Ohnishi | |
| 5,346,546 A * | 9/1994 | Kaliski | C09C 1/36 106/444 |
| 5,542,948 A | 8/1996 | Weaver et al. | |
| 6,280,702 B1 * | 8/2001 | Carter | A61K 49/006 600/101 |
| 6,599,496 B2 | 7/2003 | Carter et al. | |
| 6,815,170 B1 * | 11/2004 | Morton | G01N 33/585 435/40.5 |
| 8,709,142 B2 | 4/2014 | Story et al. | |
| 9,034,087 B2 | 5/2015 | Story et al. | |
| 11,452,783 B2 * | 9/2022 | Timm | A61K 49/006 |
| 2002/0031474 A1 | 3/2002 | Carter et al. | |
| 2013/0098265 A1 | 4/2013 | Story et al. | |
| 2016/0193365 A1 | 7/2016 | De Haas | |

FOREIGN PATENT DOCUMENTS

| | | |
|---|---|---|
| CN | 1458185 A | 11/2003 |
| CN | 1935263 A | 3/2007 |
| CN | 104971365 A | 10/2015 |
| CN | 105998065 A | 10/2016 |
| JP | H06-294081 A | 10/1994 |
| JP | 2005-521707 A | 7/2005 |
| JP | 2007-114129 A | 5/2007 |
| JP | 2007-262062 A | 10/2007 |
| WO | WO-99/44638 A1 | 9/1999 |
| WO | WO-2007/024429 A2 | 3/2007 |
| WO | WO-2007/0115291 A2 | 10/2007 |

OTHER PUBLICATIONS

"Pointer" Endoscopic Marker ADDOBIO Product Brochure; 43 pages (see pp. 7-8) which Applicant believes may have been distributed by Osteonic Co., Ltd. (see http://osteonic.com/eng/product/product_list_view.php?M1=7&M2-72&M3=74#, and https://www.accessdata.fda.gov/scripts/cdrh/cfdocs/cfRL/rl.cfm?lid=513719&lpcd-NBG), printed Nov. 2017.
Butyl Acrylate MSDS, BASF, The Chemical Company, Revision Date Oct. 26, 2005, 8 pages.
Cilurzo et al. (2011) "Injectability Evaluation: An Open Issue," AAPS PharmSciTech, 12(2): 604-609.
Combined Search and Examination Report under Sections 17 & 18(3) dated Mar. 15, 2018 in GB Patent Application No. 1802374.7, 6 pages.
Fung, et al., Introduction to Bioengineering World Scientific Publishing, p. 163, (Year: 2001).
Glycidyl methacrylate MSDS, Sigma-Aldrich.com, Revision Date Jun. 23, 2015, 9 pages
Great Britain Patent Application No. 1802374.7, Examination Report, dated Jul. 23, 2019.
International Search Report and Written Opinion in PCT/US2018/016227 dated Apr. 19, 2018, 12 pages.
Methyl methacrylate MSDS, Science Lab.com, created Oct. 10, 2005, 5 pages.
Saraswathi et al. (2013) "Polymers in Mycoadhesive Drug Delivery System—Latest Updates," Int. J. Pharm, Sci. 5(3): 423-430.

(Continued)

*Primary Examiner* — Walter E Webb
*Assistant Examiner* — Amanda Michelle Petritsch
(74) *Attorney, Agent, or Firm* — MARSHALL, GERSTEIN & BORUN LLP

(57) ABSTRACT

Provided is a tissue staining composition containing carbon particles having a mean particle diameter less than 0.3 µm in diameter (optionally less than 0.2 µm in diameter) together with one or more agents that maintain the carbon particles in suspension (for example, an anti-settling agent and/or surfactant). In certain circumstances, the anti-settling agent may also have mucoadhesive properties. The tissue staining composition is visually dark and does not disperse rapidly when introduced into regions of tissue of interest making it ideal for marking the regions that can be visualized clearly and over prolonged periods of time via, for example, direct visualization, endoscopic or laparoscopic inspection. The invention also provides methods of making and using the tissue staining composition for marking regions of tissue of interest, for example, gastrointestinal tissue, as well as other tissues.

25 Claims, 8 Drawing Sheets

(56) References Cited

OTHER PUBLICATIONS

SpotTM Endoscopic Marker, Instructions for use accessed on the internet at https://www.gi-supply.com/wp-content/uploads/2017/05/Spot-IFU-G44-006-Rev-10-no-crop.pdf; 1page, printed Nov. 2017.
SpotTM Endoscopic Marker, product literature accessed on the internet at <https://www.gi-supply.com/wp-content/uploads/2017/07/Spot-Sample-Booklet-Our-Story-G-1301-03.pdf>; 12 pages, printed Nov. 2017.
Tscharnuter et al. (2011) "ASTM Carbon Black Reference Materials: Particle Sizing Using a Brookhaven Instruments BI-DCP, Disc Centrifuge Photosedimentometer," Brookhaven Instruments Corporation, 1: 1-10.2011, downloaded from http://citeseerx.ist.psu.edu/viewdoc/download?doi=10.1.1.203.4882&rep=rep1&type=pdf on Jan. 17, 2018.
US Ink "How Does a Densitometer Work?" vol. IX, pp. 1-6, downloaded from http://www.sunchemical.com/download/how-does-a-densitometer-work/ on Jan. 17, 2018.
Wu, et al., "Sentinel Lymph Node Detection Using Carbon Nanoparticles in Patients with Early Breast Cancer," PLOS One, (2015), vol. 10, No. 8, pp. 1-12.
Xie, P. et al., Drug-loaded carbon nanoparticle suspension injection: drug selection, releasing behavior, in vitro cytotoxicity and in vivo lymph node targeting, Journal of Nanoscience and Nanotechnology. 2016, vol. 16, No. 7, pp. 6910-6918.
Yu et al. (2014) "Chapter 2. Mucoadhesion and Characterization of Mucoadhesive Properties," Mucosal Delivery of Biopharmaceuticals, pp. 35-44, J. das Neves, B. Sarmento (eds.).
SPOT Endoscopic Marker, Safety Data Sheet, GI Supply, Camp Hill, Pennsylvania, 7 pp (effective date Oct. 29, 2015).
Bonnard et al., Noir de carbone, CAS No. 1333-86-4, Institut National de Recherche et de Sécurité, 8 pp. (2007).
European Patent Application No. 18753763.4, Extended European Search Report, dated Dec. 7, 2020.
Japanese Patent Application No. 2019-507908, Office Action, issued Nov. 2, 2021.
"Black Eye" Endoscopic Marker Product Brochure (dated 2012) accessed on the internet at http://www.innomedicus.com/Files/products/gastro%20-%20black%20eye/015_30_ifu - black_eye_v03_rev1.pdf; 1 page, printed Nov. 2017.
"Black Eye" Endoscopic Marker Product Brochure (dated 2012) accessed on the internet at http://www.innomedicus.com/Files/products/gastro%20-%20black%20eye/015_30_pi - black_eye_v130305tsec.pdf; 2 pages, printed Nov. 2017.
"Endomark" Endoscopic Marker, product literature (dated Aug. 2015) accessed on the internet at http://www.pmtcorp.com/pdfs/2015_PMT_Endomark_Sell_Sheet.pdf; 2 pages, printed Jan. 23, 2018.
"Insights on Carbon Black Fundamentals," Modern Dispersions, Inc., downloaded from http://www.moderndispersions.com/carbonblack.html on Jan. 26, 2018.
"Pointer" Endoscopic Marker ADDOBIO Product Brochure; 42 pages (see pp. 7-8) which Applicant believes may have been distributed by Thoracent, Inc, (see https://www.accessdata.fda.gov/scripts/cdrh/cfdocs/cfRUrl.cfm?lid=521479&Ipcd-NBG), printed Nov. 2017.
"Pointer" Endoscopic Marker ADDOBIO Product Brochure; 43 pages (see pp. 7-8) which Applicant believes may have been distributed by Osteonic Co., Ltd. (see http://osteonic.com/eng/product/product_list_view.php?M1=7&M2-72&M3-74#, and https://www.accessdata.fda.gov/scripts/cdrh/cfdocs/cfRUrl.cfm?lid=513719&Ipcd-NBG), printed Nov. 2017.
Combined Search and Examination Report under Sections 17 & 18(3) mailed Mar. 15, 2018 in GB Patent Application No. 1802374.7, 6 pages.
Fung et al., Introduction to Bioengineering, World Scientific Publishing, p. 163 (2001).
Office Action for U.S. Appl. No. 15/690,178, dated Dec. 11, 2018.
Office Action for U.S. Appl. No. 15/690,178, dated Jul. 13, 2018.
Office Action for U.S. Appl. No. 15/690,178, dated Sep. 30, 2019.
Office Action for U.S. Appl. No. 15/690,178, dated Jul. 24, 2020.
Office Action for U.S. Appl. No. 15/690,178, dated Feb. 18, 2022.

* cited by examiner

S = Carbon particle containing solution was sonicated to give a median particle size of <0.2μm, NS = Carbon particle containing solution was not sonicated where carbon particles had a median particle size of about 6.6μm.

S = Carbon particle containing solution was sonicated to give a median particle size of <0.3μm, NS = Carbon particle containing solution was not sonicated where carbon particles had a median particle size of about 6.6μm.

S = Carbon particle containing solution was sonicated to give a median particle size of <0.3μm, NS = Carbon particle containing solution was not sonicated where carbon particles had a median particle size of about 6.6μm.

S = Carbon particle containing solution was sonicated to give a median particle size of <0.3μm, NS = Carbon particle containing solution was not sonicated where carbon particles had a median particle size of about 6.6μm.

TISSUE STAIN AND USE THEREOF

CROSS REFERENCE TO RELATED APPLICATIONS

This application is a continuation application of U.S. patent application Ser. No. 15/690,178 filed Aug. 29, 2017 which claims the benefit of, and priority to, U.S. Provisional Patent Application Ser. No. 62/458,805 filed Feb. 14, 2017, which are is hereby incorporated by reference herein in their entirety.

FIELD OF THE INVENTION

The invention relates generally to a tissue staining composition for marking regions of living tissue, for example, regions of the gastrointestinal tract, in order to identify and visualize the regions at a later point in time.

BACKGROUND

In certain medical procedures there is a need to mark regions of tissue (for example, cancerous or pre-cancerous lesions) so that they can then be later identified, for example, via endoscopic, laparoscopic, or open surgical procedures, weeks, months or years later. Such markings can identify tissue to be surgically excised via a subsequent procedure or permit a physician or other medical provider to assess whether cytological or morphological changes have occurred over time that may justify medical intervention (for example, surgery or drug treatment) to remove or treat the tissue in question.

This type of marking and monitoring is routine in the field of gastroenterology. For example, during an endoscopic examination of the gastrointestinal tract, a physician or other medical practitioner may wish to mark an abnormal area or potential lesion for subsequent monitoring and/or surgical intervention. In a marking procedure, a staining composition is injected through the luminal mucosal surface of the gastrointestinal tract into the submucosal tissue. However, existing stains (e.g., methylene blue, indigo carmine, indocyanine green-based stains) may be difficult to visualize endoscopically even at the time of injection into tissue of interest because the stain may leak or diffuse out of the tissue at the point of entry and thus visually obscure the area being marked. Furthermore, even after injection, it may become difficult to identify the marked regions months to years later because the marks may fade or even disappear over time. In other words, such stains may not facilitate permanent marking of tissue to accommodate accurate, long term tracking of tissue of interest. As a result, it can be difficult or even impossible for a physician or other medical practitioner to monitor with confidence abnormal tissue, pre-cancerous or cancerous lesions over time. There are similar needs for monitoring other tissues of interest, for example, in the bladder, urinary tract, breast, lymph nodes, central and peripheral nervous system, and lungs.

Furthermore, it has been observed that with certain tissue stains, the staining agents, if particulate, may settle out of solution over time. As a result, the instructions for use typically require that the tissue stain be shaken or vortexed so that the staining agents are resuspended or redistributed prior to use to ensure adequate marking. However, this step may not be performed adequately, if at all, prior to injection, and as a result differing amounts of staining agent may be delivered during different marking procedures or when different areas are marked during the same procedure, resulting in inconsistent marks or marks where insufficient staining agent has been introduced to create a durable mark.

Furthermore, certain stains (e.g., india ink) often contain impurities such as shellacs, phenols, ammonia, and animal products. These impurities can be associated with complications such as inflammatory reactions or may even be carcinogens.

Despite the advances made in tissue marking agents, for example, endoscopic tissue marking agents, to date, there is still an ongoing need for agents with improved marking reliability, durability, and safety.

SUMMARY OF THE INVENTION

It has been discovered that it is possible to produce a biocompatible, carbon particle-based tissue staining composition that is easy and reliable to use, is easily observable during injection into tissue, and provides a durable, reliable mark that can be visualized over time, either by direct observation or by inspection using an endoscope, laparoscope or other similar device. This has been facilitated by the discovery that, when using carbon particles as the staining agent, the carbon particles should have a mean particle diameter less than 0.3 µm in diameter (for example, less than 0.2 µm in diameter) to enhance the darkness of the staining agent. Depending upon the presence of an agent, such as a surfactant, such as a non-ionic surfactant, present in an amount sufficient to reduce particle agglomeration, the particles may remain in suspension for prolonged periods of time with little or no sedimentation (settling). However, the composition may also comprise an anti-settling agent and/or a mucoadhesive agent. Under certain circumstances, a single agent can act as both an anti-settling agent and a mucoadhesive agent. The tissue staining compositions described herein have improved storage characteristics because the carbon particles are less likely to settle out of solution upon storage, provide the same uniform optical density throughout a marking procedure, are darker than other commercially available carbon particle-based tissue stains and thus are easier to visualize at the time of injection into a region of tissue of interest, and provide a durable mark at the region that can be more readily visualized over time. In addition, the tissue staining composition can be thermally sterilized, for example, by autoclaving, because the formulation of the tissue stain is heat stable.

In one aspect, the invention provides a liquid, tissue staining composition comprising: carbon particles at a concentration of from about 0.025% to about 2.0% (w/v) having a mean particle diameter of less than 0.3 µm in diameter (e.g., less than 0.2 µm in diameter); an optional anti-settling agent (ASA), for example, an ASA selected from the group consisting of hydroxyethyl cellulose, hydroxypropyl cellulose, dextran, and guar gum at a concentration of from about 0.025% to less than 5.0% (w/v) (for example, from about 0.05% to less than 5.0% (w/v), from about 0.05% to about 1.0% (w/v), from about 0.1% to about 1.0% (w/v), or from about 0.1% to about 0.5% (w/v)); and an optional mucoadhesive agent.

In another aspect, the invention provides a liquid, tissue staining composition comprising: carbon particles at a concentration of from about 0.025% to about 2.0% (w/v) having a mean particle diameter of less than 0.3 µm in diameter (e.g., less than 0.2 µm in diameter); an anti-settling agent (ASA), for example, an ASA selected from the group consisting of hydroxyethyl cellulose, hydroxypropyl cellulose, dextran, and guar gum at a concentration of from about 0.025% to less than 5.0% (w/v) (for example, from about 0.05% to less than 5.0% (w/v), from about 0.05% to about 1.0% (w/v), from about 0.1% to about 1.0% (w/v), or from about 0.1% to about 0.5% (w/v)); and an optional mucoadhesive agent.

In certain embodiments, and with regard to each of the foregoing aspects, the carbon particles have a mean particle diameter less than 0.2 µm, for example, from about 0.05 µm to less than 0.2 µm. Furthermore, in certain embodiments, the composition can be characterized in that, when centrifuged for 60 minutes at 5,000×g, less than 50% of the carbon particles settle out of solution.

The carbon particles can be derived from carbon black, activated carbon, unactivated carbon or a combination thereof. The carbon particles preferably have a level of polycyclic aromatic hydrocarbons of no greater than 0.5 ppm based on the total amount of carbon particles. Preferably the carbon particles are depyrogenated or are otherwise pyrogen free. This can be achieved, for example, by heating carbon powder at 220° C. for 1 hour to produce pyrogen free dry carbon.

In certain embodiments, the ASA is also a mucoadhesive agent (or has mucoadhesive properties). Exemplary ASAs with mucoadhesive properties include, for example, hydroxyethyl cellulose, hydroxypropyl cellulose, dextran, and guar gum.

In another embodiment, the composition further comprises a viscosity-increasing agent. The viscosity-increasing agent can be present at a concentration of from about 5% to about 25% (w/v). Exemplary viscosity-increasing agents include, for example, glycerol, propylene glycol, isopropylene glycol, polyethylene glycol, cellulose and combinations thereof.

In another embodiment, the composition further comprises an anti-foaming agent. In certain embodiments, the anti-foaming agent can be present at a concentration of from about 0.005% to about 1.0% (w/v). Exemplary anti-foaming agents include, for example, dimethicone and simethicone and combinations thereof.

In another embodiment, the composition further comprises a surfactant, for example, a non-ionic surfactant. In certain embodiments, the surfactant can be present at a concentration of from about 0.01% to about 2.0% (w/v). Exemplary surfactants include, for example, pharmaceutically acceptable polyoxyethylene sorbitan esterified with a fatty acid, for example, Tween® such as Tween® 80.

In another embodiment, the composition further comprises a preservative, for example, benzyl alcohol, methyl or ethyl paraben, and benzalkonium chloride. In certain embodiments, the preservative can be present at a concentration of from about 0.01% to about 4.0% (w/v).

In certain embodiments, the composition, for example, for use in gastrointestinal applications, is capable of passing through a 25 gauge needle about 240 cm in length upon application of a force no greater than about 32N (for example, from about 22 to 32N, or about 22N or less, or about 10N or less) to push the composition through the needle. In certain other embodiments, the composition, for example, for use in breast cancer tissue marking, is capable of passing through a 14 gauge needle about 5 cm in length upon application of a force no greater than about 32N (for example, from about 22 to 32N, or about 22N or less, or about 10N or less) to push the composition through the needle.

In another embodiment, the composition comprises from about 0.025% to about 2.0% (w/v) carbon particles or from about 0.1% to about 2.0% (w/v) carbon particles; optionally, and when present, from 0.025% to less than 5.0% (w/v) of an ASA selected from the group consisting of hydroxyethyl cellulose, hydroxypropyl cellulose, dextran, and guar gum; optionally, and when present, from about 5.0% to about 25% (w/v) viscosity-increasing agent; from about 0.005% to about 1.0% (w/v) anti-foaming agent; and from about 0.1% to about 2.0% (w/v) surfactant. In another embodiment, the composition comprises from about 0.025% to about 1.0% (w/v) carbon particles or from about 0.1% to about 1.0% (w/v) carbon particles; optionally, and when present, from about 0.025% to about 1.0% (w/v) of an ASA selected from the group consisting of hydroxyethyl cellulose, hydroxypropyl cellulose, dextran, and guar gum; optionally, and when present, from about 12% to about 18% (w/v) of a viscosity-increasing agent; from about 0.05% to about 0.25% (w/v) anti-foaming agent; and from about 0.7% to about 1.5% (w/v) surfactant. Each of the foregoing compositions may further comprise a preservative, for example, benzyl alcohol.

It is contemplated that the staining composition can be produced by combining sterile agents to one another so that the resulting staining composition is sterile. However, in another approach, once the tissue staining composition has been prepared, it can be sterilized, for example, by filter sterilization, by exposure to one or more sterilizing agents, separately or in combination, such as exposure to high temperature and/or high pressure (for example, during autoclaving), or by exposure to ionizing radiation. Alternatively, the tissue staining composition after inclusion in a delivery device (e.g., a vial, syringe, etc.) can be sterilized using one or more procedures known and used in the art of sterilization, for example, by exposure to one or more sterilizing agents, separately or in combination, such as exposure to high temperature and/or high pressure (for example, during autoclaving), or by exposure to ionizing radiation. The sterilization process preferably achieves a sterility assurance level (SAL) of $10^{-3}$ or better; i.e. the probability of any given unit of product being non sterile after the process is no more than 1 in $10^3$. More preferably, the sterilization process achieves an SAL of $10^{-4}$ or better, $10^{-5}$ or better, $10^{-6}$ or better, or $10^{-7}$ or better.

In another aspect, the invention provides a method of preparing the foregoing tissue staining composition, the method comprising: (a) producing a composition comprising carbon particles, preferably depyrogenated carbon particles, having a mean particle diameter of less than 0.3 µm or less than 0.2 µm in diameter; and (b) combining the composition comprising the carbon particles with an optional ASA, and an optional mucoadhesive agent and/or one or more other excipients to produce the tissue staining composition. During step (a), the carbon particles preferably are combined with a surfactant and an anti-foaming agent prior to a deagglomeration procedure that produces carbon particles to give a mean particle diameter of less than 0.3 µm or less than 0.2 µm. For example, the carbon particles produced in step (a) can be produced by sonicating or homogenizing carbon particles (which include carbon primary particles, aggregates, and agglomerates) having a mean particle diameter of, for example, greater than 5.0 µm in diameter to produce carbon particles having a mean particle diameter of less than 0.3 µm or less than 0.2 µm in diameter.

The resulting composition can be sterilized, for example, by filter sterilization, autoclaving or exposure to ionizing radiation. Furthermore, when the composition is introduced into a delivery device, the resulting device can be terminally sterilized by using one or more of the sterilization approaches described herein.

In another aspect, the invention provides a method of staining a region of tissue in a subject, the method comprising injecting the foregoing tissue staining composition into the region of interest in the subject in an amount effective to stain the region so as to be visible by visual inspection, for example, by the unaided eye, an endoscope, laparoscope or other device.

In one embodiment, the tissue is present in the gastrointestinal tract, bladder, breast, lymph nodes, lung, or central or peripheral nervous system of the subject. In certain embodiments, the tissue is present in the gastrointestinal tract of the subject.

In another embodiment, the stain is visible, for example, visible endoscopically, for at least 6 months, 12 months, 24 months, 36 months, 48 months, 60 months, or 120 months after the staining of tissue.

These and other aspects and features of the invention are described in the following detailed description and claims.

BRIEF DESCRIPTION OF THE DRAWINGS

The foregoing and other objects, features and advantages of the invention will become apparent from the following description of preferred embodiments, as illustrated in the accompanying drawings. Like referenced elements identify common features in the corresponding drawings. The drawings are not necessarily to scale, with emphasis instead being placed on illustrating the principles of the present invention, in which.

DETAILED DESCRIPTION

The invention is based at least, in part, upon the discovery that it is possible to produce a biocompatible, carbon particle-based tissue stain that is reliable to use, easily observable during injection into tissue, and provides a durable, reliable mark that can be visualized over time, either by direct observation or by endoscopic or laparoscopic inspection. This has been facilitated by the discovery that, when using carbon particles as the staining agent, it is important to use carbon particles that have a mean particle diameter less than 0.3 µm (for example, less than 0.2 µm in diameter) to enhance the darkness of the staining agent.

Depending upon the presence of an agent that reduces or eliminates carbon particle agglomeration (for example a surfactant, such as a non-ionic surfactant), the carbon particle may remain in suspension for prolonged periods of time with little or no sedimentation (settling). However, depending upon the circumstances, the composition may also comprise an anti-settling agent and/or a mucoadhesive agent. A single agent can have both anti-settling and mucoadhesive properties. The resulting tissue stain is much darker than comparable carbon particle-based tissue stains that contain a larger amount of carbon particles where the carbon particles have a larger mean particle diameter. As a result, the tissue stains of the invention are easier to visualize at the time of injection into a region of tissue of interest, and provide a durable mark at the region that can be visualized over time. Furthermore, the resulting tissue stain has improved handling and storage characteristics because the carbon particles are less likely to settle out of solution upon storage and can be easily in injected into tissues of interest using commercially available needles and injection systems.

The terms "tissue stain," "tissue staining composition," and "tissue marking composition" are used interchangeably herein.

Figure 1:
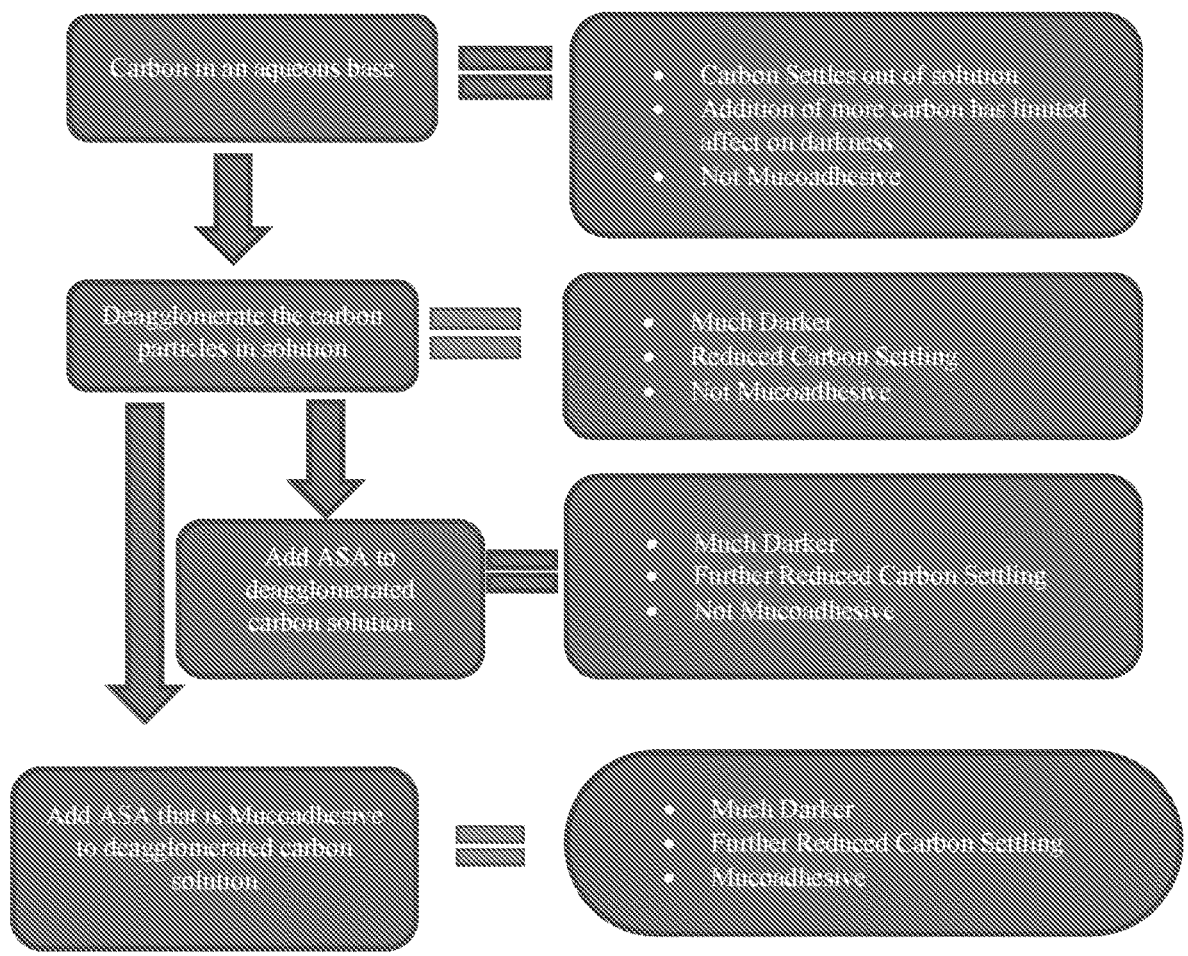
FIG. 1 illustrates the development and features of exemplary staining solutions of the invention.

The properties and advantages of the carbon partible-based tissue staining compositions of the invention are shown schematically in FIG. 1. In particular, the tissue staining compositions of the invention (i) are much darker (achieved by reducing the size of the carbon particles) and thus are easier to visualize upon introduction into the tissue of interest and then produce a durable mark that can be visualized over time, (ii) exhibit reduced settling of the carbon particles (achieved by reducing the particle size and optionally by adding an anti-settling agent) and thus are easier to manipulate by the user, and (iii) are mucoadhesive (achieved by adding a mucoadhesive agent and/or by using an anti-settling agent with mucoadhesive properties) and thus are contemplated to be easier to visualize upon introduction into a tissue of interest with less "bleeding" of the stain out of the site of introduction and produce a durable mark that can be visualized over time.

The tissue stains of the invention can be easily visualized as the stain is being injected into a region of tissue of interest, and when introduced, given the darkness and the optional mucoadhesive properties of the tissue stain, the stain can be visualized, for example, by direct observation or by a medical instrument, for example, endoscope or laparoscope, over a prolonged period of time, for example, for weeks, months or years. The tissue stains are particularly useful when a physician or other medical practitioner wishes to mark a tissue for subsequent surgery or to monitor a region of a tissue over time, for example, to assess whether potentially abnormal tissue has become pre-cancerous or cancerous.

For example, if a cancerous or precancerous lesion is found in the gastrointestinal tract, urinary bladder, bronchi of the lungs, breast tissue, or lymph nodes or in other locations, a marking at the site can be used to guide a surgeon to that site in a subsequent procedure. By way of example, polyps in the colon typically are removed promptly because of their potential for malignancy. Polyps are discrete mass lesions that protrude into the intestinal lumen. Mucosal neoplastic (adenomatous) polyps give rise to adenocarcinoma of the colon and therefore, polyps detected at sigmoidoscopy or barium enema are removed as soon as possible by colonoscopic polypectomy or other techniques such as those described in U.S. Pat. Nos. 5,122,147 and 5,542,948. Sometimes polyps or tumors cannot be safely or completely removed by colonoscopy, and surgical resection must follow. Once the polyps have been removed, surveillance colonoscopy is periodically repeated to look for missed polyps, new adenomas, and residual or recurrent cancer.

It is understood that the tissue staining compositions can be used to mark a variety of tissues in a subject, for example, tissues in the gastrointestinal tract, the breast, the lymph nodes, the bladder and urinary tract, etc. However, as discussed in more detail below, a particular tissue staining formulation can be optimized for delivery to and/or staining a tissue of interest.

I. Carbon Particles

The tissue marking composition of the invention includes carbon particles as a source of pigment. Although the intensity of the color (darkness) can be increased by increasing the concentration of carbon particles in suspension, it has also been discovered that reducing the particle size can have an even more profound effect on the darkness of the suspension. As a result, by reducing particle size, for example, by deagglomeration, it is possible to produce staining compositions that are much darker than comparable staining compositions with much higher concentrations of particles that are larger in size. This feature is demonstrated in FIGS. 2, 5, 6 and 8. The reduction in the particle size may also reduce the rate of settling of the particles in solution. Furthermore, depending upon the size of the particles example, particles having a mean particle diameter less than 0.3 µm, or preferably less than 0.2 µm) and the presence of an agent, for example, a surfactant (for example, a non-ionic surfactant) that reduces or prevents reagglomeration of the carbon particles, it may be possible to produce a stain where the carbon particles remain in suspension for a prolonged period of time. Although filtering of particles can reduce the size of the particles included in the formulation, it does not actually change the size of the agglomerates and the minimum size of the particles is limited by the size of the filter.

As used herein, the term "carbon particles" is understood to mean individual carbon particles (primary carbon particles) as well as aggregates of individual carbon particles where the aggregates of smaller particles are bound together strongly enough to behave as a single particle, both of which have a particle size that cannot be reduced by exposure to mechanical forces and/or energy, for example, by sonication or homogenization, for example, by using the procedures described herein. Individual carbon particles and/or aggregates may be held together by weak bonds (for example, van der Waals forces) to form agglomerates that can be broken by the addition of mechanical forces and/or energy (for example, via sonication or homogenization) to produce predominantly individual carbon particles, aggregates and combinations thereof (e.g., agglomerates having a mean diameter greater than 5 µm represent less than 30%, 20%, 10%, or 3%, 2% or 1% of the composition).

In certain embodiments, the carbon particles, which optionally have been exposed to a deagglomeration process, have a mean particle diameter less than 0.3 µm in diameter, for example, less than 0.2 µm in diameter. In the tissue staining compositions of the invention, the carbon particles (which can be primary carbon particles, aggregates of carbon particles, or a combination thereof) have a mean particle diameter less than 0.3 µm in diameter, preferably less than 0.2 µm in diameter. The size of the carbon particles can be measured using techniques known in the art such as by dynamic light scattering, laser light scattering particle size analysis or by disc centrifuge analysis. The carbon particles may have a mean particle diameter in the range from about 0.1 µm to less than 0.3 µm. In certain embodiments, the carbon particles have a mean particle diameter in the range from about 0.1 µm to about 0.2 µm. In certain embodiments, the carbon particles have a mean particle diameter in the range from about 0.15 µm to about 0.2 µm. In certain embodiments, the mean particle diameter is less than 0.2 µm.

In certain embodiments, the carbon particles have a mean diameter in the range from about 0.01 µm to less than 0.3 µm, from about 0.01 µm to less than 0.25 µm, from about 0.01 µm to less than 0.2 µm, from 0.01 µm to less than 0.15 µm.

In certain embodiments, the carbon particles have a mean diameter from about 0.05 µm to 0.25 µm or less, from about 0.05 µm to 0.2 µm or less (for example, from 0.05 µm to 0.19 µm, from 0.05 µm to 0.18 µm, from 0.05 µm to 0.17 µm, from 0.05 µm to 0.16 µm, from 0.05 µm to 0.15 µm, from 0.05 µm to 0.14 µm, from 0.05 µm to 0.13 µm, from 0.05 µm to 0.12 µm, from 0.05 µm to 0.11 µm, or from 0.05 µm to 0.1 µm). In certain embodiments, the carbon particles have a mean diameter from about 0.08 µm to 0.2 µm or less (for example, from 0.08 µm to 0.19 µm, from 0.08 µm to 0.18 µm, from 0.08 µm to 0.17 µm, from 0.08 µm to 0.16 µm, from 0.08 µm to 0.15 µm, from 0.08 µm to 0.14 µm, from 0.08 µm to 0.13 µm, from 0.08 µm to 0.12 µm, from 0.08 µm to 0.11 µm, or from 0.08 µm to 0.1 µm). In certain embodiments, the carbon particles have a mean diameter from 0.1 µm to 0.2 µm or less (for example, from 0.1 µm to 0.19 µm, from 0.1 µm to 0.1.8 µm, from 0.1 µm to 0.17 µm, from 0.1 µm to 0.16 µm, from 0.1. µm to 0.15 µm, from 0.1 µm to 0.14 µm, from 0.1 µm to 0.13 µm, or from 0.1 µm to 0.12 µm, or from 0.1 µm to 0.11 µm).

Carbon particles can be derived from carbon black, charcoal, or coke. Carbon black is finely divided carbon such as vaporized heavy oil fractions produced by burning hydrocarbons using partial oxidation. The pigment can contain over 97% carbon. The oil furnace process represents the most widely used method for producing carbon black. Generally, a liquid hydrocarbonaceous feedstock is sprayed into turbulent products of combustion produced by reacting fluid fuel and oxygen and the hydrocarbon feedstock is converted into carbon black which is separated from combustion gases. Carbon black can also be produced by burning natural gas and letting the flame impinge on a cool surface. The preferred carbon black useful herein is low in incompletely burned hydrocarbons which may be absorbed during manufacture; particularly, the carbon black is low in aromatics and other compounds which may be carcinogens. More particularly, the preferred carbon black is low in residual polycyclic aromatic hydrocarbons. By "low" is meant substantially non-carcinogenic levels. In a preferred embodiment, the carbon black has a level of polycyclic aromatic hydrocarbons of not greater than 0.5 ppm based on the amount of carbon black.

Charcoal can be prepared by the ignition of wood, sugar, and other carbon-containing compounds in the absence of air. It has a graphitic structure but is not well developed in crystallinity. It will therefore be categorized as amorphous herein. Activated carbon is similar obtained by the carbonization or destructive distillation of vegetable matter, e.g., wood, nut shells, bones, or other carbonaceous material. The carbon is activated by heating to high temperatures in the presence of water or carbon dioxide which results in a carbon having a porous internal structure. Carbon which has not been subjected to this treatment will be called unactivated herein. Coke is prepared by heating coal in the absence of air.

Exemplary carbon particles, preferably 4750 Monarch, can be obtained from Cabot Corp., Billerica, MA or Asbury Carbon 5388 or 5377 obtained from Asbury Carbons, Asbury, NJ.

The density of the carbon particles typically used in the tissue staining composition of the invention is from about 1.7 g/cm$^3$ to about 1.9 g/cm$^3$, which is greater than the density of water either alone or with glycerol. As a representative formulation vehicle, the density of water containing 25% (w/v) glycerol is not appreciably greater than 1.0 g/cm$^3$. Due to the higher density of the carbon particles than the liquid phase, the carbon particles typically settle out to some degree, resulting in a liquid portion and a settled solid portion, such that the liquid portion has a lower number of carbon particles compared with the original composition as a whole. A reduced amount of carbon particles can lead to poorer marking performance of the liquid portion of the composition. Such solutions should be shaken, vortexed or otherwise mixed prior to use. Given that some users may not redistribute the staining agent (for example, by shaking) prior to use, it is desirable to reduce the amount of settling of the carbon particles over time. Methods for reducing settling include reducing the particle size, either alone or in combination with increasing the liquid viscosity of the composition and/or including an anti-settling agent. It has been discovered that the rate of settling of the carbon particles can be slowed significantly by reducing the mean particle diameter (including aggregates) to less than 0.3 µm in diameter (for example, less than 0.2 µm in diameter) and optionally including an anti-settling agent (see, FIGS. 3 and 4).

Typically carbon is available as primary carbon particles, aggregates, agglomerates, and combinations thereof. The primary carbon particles and the aggregates cannot be reduced in size, for example, by the application of mechanical forces and/or energy, for example, via sonication or homogenization. Given that the carbon often comprises agglomerates (for example, agglomerates having a mean particle diameter greater than 5 µm) the agglomerates can be broken down by a deagglomeration process to liberate individual carbon particles and/or aggregates. When the attractive forces that hold the agglomerates together are disrupted, for example, mechanically and/or through application of energy, the resulting carbon particles can have a mean particle diameter less than 0.3 µm, for example, less than 0.2 µm, or have a mean particle diameter in a range of from about 0.1 to about 0.2 µm, or have a mean diameter in a range of from about 0.05 µm to less than 0.2 µm. The smaller particles appear much darker than a comparable weight of larger particles. Without wishing to be bound by theory, it is believed that the visibility of a given weight of carbon particles diminishes as the particles became larger, because the eye observes fewer large particles as being less black than the same weight of more numerous smaller carbon particles, due to the larger "spaces" between the larger particles. Thus, deagglomeration can increase the visibility of the mark, as well as reduce the amount and speed of settling. The size of the particles can be determined by using a number of approaches including, for example, laser light scattering particle analysis (LLSPA) (also known as laser diffraction or laser diffractometry), and dynamic light scattering (DLS). LLSPA may be more accurate when analyzing larger particles (for example, particles having a mean diameter of about 5 µm or greater) whereas DLS may be more accurate when analyzing smaller particles (for example, particles having a mean diameter of 0.5 µm or less). In addition, particle sizes can be measured using a LUMiSizer 650 that employs Space- and Time-resolved Extinction Profiles (STEP) technology, which measures particles in the range of, for example, 20 nm to 100 µm.

The darkness of the tissue staining compositions containing the carbon particles can be measured as a function of absorbance or reflectance by means of a densitometer or uv/visible spectrophotometer, such as an X Rite 504 Portable Color Reflection Spectrodensitometer and a Thermo Scientific Biomate S3 UV-Vis spectrophotometer and the darkness may be expressed in terms of % Absorbance, % Reflectance, or optical density.

The deagglomeration process can be achieved by sonication, homogenization, high shear mixing, or ball milling, or other approaches to reduce particle size. Preferably, deagglomeration is achieved by sonication or homogenization. In certain embodiments, the carbon is deagglomerated by sonication in a 350W Biologics Model 3000 Ultrasonic Homogenizer with Solid Titanium Tip ½" Diameter unit from BioLogics, Inc., Manassas, VA sonicator on 60% power, for about 3 minutes or until approximate particle size is achieved. In other embodiments, the carbon is deagglomerated by homogenization, for example, by homogenizing at approximately 8,500 rpm for about 1 hour (for example, using a Silverson Model L5M-A mixer-homogenizer) or until the approximate particle size is achieved. One exemplary approach for deaggregating carbon particles by homogenization is described in Example 2.

In certain embodiments, the carbon particles are deagglomerated before they are mixed with other excipients, for example, the ASA and the optional mucoadhesive agent, because the process of deagglomeration may result in viscosity changes to ASA and the mucoadhesive agent, especially if the ASA or mucoadhesive agent are fabricated from or otherwise contain polymers which can be altered by high shear conditions. The carbon particles may be maintained as aggregates having a mean particle diameter less than 0.3 µm (for example, less than 0.2 µm) by the inclusion of additional additives, for example, one or more surfactants described below, which prevent or slow down the rate of reagglomeration due to van der Waals attraction.

Preferably the carbon particles are depyrogenated or are otherwise pyrogen free. This can be achieved, for example, by heating carbon powder at 220° C. for 1 hour to produce pyrogen free dry carbon.

Depending upon the intended application, the final concentration of carbon in the tissue staining composition can be from about 0.025% (w/v) to about 2.0% (w/v), from about 0.025% (w/v) to about 1.5% (w/v), from about 0.025% (w/v) to about 1.0% (w/v), from about 0.025% (w/v) to about 0.75% (w/v), from about 0.025% (w/v) to about 0.5% (w/v), 0.1% (w/v) to about 2.0% (w/v), from about 0.1% (w/v) to about 1.5% (w/v), from about 0.1% (w/v) to about 1.0% (w/v), from about 0.1% (w/v) to about 0.75% (w/v), from about 0.1% (w/v) to about 0.5% (w/v), from about 0.25% (w/v) to about 2.0% (w/v), from about 0.25% (w/v) to about 1.5% (w/v), from about 0.25% (w/v) to about 1.0% (w/v), from about 0.25% (w/v) to about 0.75% (w/v), from about 0.25% (w/v) to about 0.5% (w/v), from about 0.5% (w/v) to about 2.0% (w/v), from about 0.5% (w/v) to about 1.5% (w/v), from about 0.5% (w/v) to about 1.0% (w/v), from about 0.5% (w/v) to about 0.75% (w/v), from about 0.75% (w/v) to about 2.0% (w/v), from about 0.75% (w/v) to about 1.5% (w/v), from about 0.75% (w/v) to about 1.0% (w/v), from about 1.0% (w/v) to about 2.0% (w/v), or from about 1.0% (w/v) to about 1.5% (w/v).

In certain preferred embodiments, the final concentration of carbon, preferably deagglomerated carbon present in the tissue staining composition ranges from about 0.25% (w/v) to about 0.5% (w/v). However, when a darker mark is desired, the final concentration of carbon present can be increased to a range from about 0.5% (w/v) to about 1.0% (w/v).

II. Anti-Settling Agents (ASAs)

In addition to agents (for example, surfactants, such as non-ionic surfactants) that reduce or prevent the reagglomeration of the carbon particles, the tissue marking compositions optionally may also include an anti-settling agent (ASA) to aid in preventing or reducing the settling of the carbon particles. Many ASAs are available, however they may be incompatible with other ingredients in the composition and/or the methods of making or sterilizing the composition. Preferred ASAs are thermally stable, for example, to facilitate sterilization by autoclaving, and should reduce the settling speed of carbon particles having a mean particle diameter of less than 0.3 µm in diameter (for example, less than 0.2 µm in diameter).

Given their lack of thermal stability in water-based solution under autoclaving conditions, hydroxypropylmethyl cellulose, non-crosslinked hyaluronic acid, xanthan, pectin, tragacanth gum, and polyvinylpyrrolidone should not be included in the composition if it is going to be sterilized by autoclaving. Suitable ASAs for use in the composition which can be sterilized by autoclaving include hydroxyethyl cellulose, hydroxypropyl cellulose, dextran, and guar gum. Hydroxyethyl cellulose, hydroxypropyl cellulose, dextran, and guar gum also have mucoadhesive properties (see, TABLES 3 and 4).

Exemplary hydroxyethyl cellulose (HEC), includes hydroxyethyl cellulose having a molecular weight of approximately $1.0 \times 10^6$ Da with a viscosity of approximately 2000 cp at 1% (w/v) (HEC2K) and hydroxyethyl cellulose having a molecular weight of approximately $1.3 \times 10^6$ Da with a viscosity of approximately 5000 cp at 1% (w/v) (HEC5K), which can be obtained from Spectrum Chemical or Ashland. Exemplary hydroxypropyl cellulose (HPC), includes hydroxypropyl cellulose having a molecular weight of approximately $8.5 \times 10^5$ Da with a viscosity of approximately 4950 cp at 5% (w/v), which can be obtained from Spectrum Chemical or Ashland.

The concentration of the ASA in the final product can range from about 0.025% (w/v) to less than 5.0% (w/v), from about 0.025% (w/v) to about 2.0% (w/v), from about 0.025% (w/v) to about 1.5% (w/v), from about 0.025% (w/v) to about 1.0% (w/v), from about 0.025% (w/v) to about 0.75% (w/v), from about 0.025% (w/v) to about 0.5% (w/v), from about 0.05% (w/v) to about 1.5% (w/v), from about 0.05% (w/v) to about 1.0% (w/v), from about 0.05% (w/v) to about 0.75% (w/v), from about 0.05% (w/v) to about 0.5% (w/v), from about 0.075% (w/v) to about 1.5% (w/v), from about 0.075% (w/v) to about 1.0% (w/v), from about 0.075% (w/v) to about 0.75% (w/v), from about 0.075% (w/v) to about 0.5% (w/v), from about 0.1% (w/v) to about 1.5% (w/v), from about 0.1% (w/v) to about 1.0% (w/v), from about 0.1% (w/v) to about 0.75% (w/v), from about 0.1% (w/v) to about 0.5% (w/v), from about 0.5% (w/v) to about 2.0% (w/v), from about 0.5% (w/v) to about 1.5% (w/v), from about 0.5% (w/v) to about 1.0% (w/v), from about 0.5% (w/v) to about 0.75% (w/v), from about 0.75% (w/v) to about 2.0% (w/v), from about 0.75% (w/v) to about 1.5% (w/v), from about 0.75% (w/v) to about 1.0% (w/v), from about 1.0% (w/v) to about 2.0% (w/v), or from about 1.0% (w/v) to about 1.5% (w/v).

As shown in Example 2, the combination of such ASAs with carbon particles having mean particle diameter of less than about 0.3 µm can result in much slower settling rates than other carbon particle-based liquid endoscopic tissue staining compositions. Settling is a process that takes place over time, and may proceed over a period of minutes, hours, days, months, or years. It is possible to quantify the rate of settling using a variety of approaches, for example, via centrifugation to accelerate the settling process. Similarly, the rate of settling, as well as particle size analysis, can be determined using a LUMiSizer 650 available from LUM GmbH, Berlin, Germany.

As a comparative method of analyzing the settling properties of a composition, a composition of interest may be subjected to centrifugal forces many times the force of gravity which allows the simulation of months of settling to occur in minutes to hours. Centrifugation of a tube containing a sample of interest may result in settling of the carbon particles at the bottom of the tube leaving a liquid depleted of carbon particles at the upper most regions of the liquid. A portion of the liquid in the upper most regions of the liquid (for example, the upper third portion) can then be analyzed to determine the amount of carbon particles that have settled. In certain embodiments, the staining composition can be characterized in that, when subjected to centrifugation for 60 minutes at 5,000×g, the staining composition, which includes the ASA, exhibits less than 70%, less than 60%, less than 50%, less than 40%, less than 30%, or less than 20% of the settling when compared against similar composition where the particles have a mean particle diameter greater than 5 µm and/or the composition lacks an ASA.

III. Mucoadhesives

Depending upon the choice of the ASA (for example, an ASA that does not also have mucoadhesive properties), it may be preferable to include an additional mucoadhesive agent. The mucoadhesive agent can aid the adherence of the staining agent in the marking of the composition to the target tissue. Without wishing to be bound by theory, it is contemplated that greater mucoadhesion promotes cohesion of the mark and, therefore, increases the likelihood that the mark will remain in one place and be more readily visible near the area of interest, potentially by reducing spreading of the pigment over time. Furthermore, it is also believed that increased cohesion may reduce the leakage associated with marking solutions post injection, such leakage being undesirable as it can cloud the field of view of an endoscope and require an operating physician to rinse the area being viewed.

Preferred mucoadhesive agents optionally are thermally stable, compatible with other components in the formulation and increase the mucoadhesion of carbon particles with a mean particle diameter of less than 0.3 µm in diameter. Exemplary mucoadhesive agents are described in Saraswathi et al. (2013) INT. J. PHARM. PHARM. SCI. 5:423-430. Exemplary mucoadhesive agents can be selected from the group consisting of hydroxyethyl cellulose, hydroxypropyl cellulose, hydroxypropylmethyl cellulose, collagen, gelatin, albumin, alginate, chitosan, dextran, guar gum, polyethylene glycol (for example, polyethylene glycol 200,000-400,000 daltons), polylactic acid, and polyglycolic acid.

The mucoadhesives can be present in the staining composition at a final concentration of from about 0.025% (w/v) to less than 5.0% (w/v), from about 0.025% (w/v) to about 2.0% (w/v), from about 0.025% (w/v) to about 1.5% (w/v), from about 0.025% (w/v) to about 1.0% (w/v), from about 0.025% (w/v) to about 0.75% (w/v), from about 0.025% (w/v) to about 0.5% (w/v), from about 0.05% (w/v) to about 1.5% (w/v), from about 0.05% (w/v) to about 1.0% (w/v), from about 0.05% (w/v) to about 0.75% (w/v), from about 0.05% (w/v) to about 0.5% (w/v), from about 0.075% (w/v) to about 1.5% (w/v), from about 0.075% (w/v) to about 1.0% (w/v), from about 0.075% (w/v) to about 0.75% (w/v), from about 0.075% (w/v) to about 0.5% (w/v), from about 0.1% (w/v) to about 1.5% (w/v), from about 0.1% (w/v) to about 1.0% (w/v), from about 0.1% (w/v) to about 0.75% (w/v), from about 0.1% (w/v) to about 0.5% (w/v), from about 0.5% (w/v) to about 2.0% (w/v), from about 0.5% (w/v) to about 1.5% (w/v), from about 0.5% (w/v) to about 1.0% (w/v), from about 0.5% (w/v) to about 0.75% (w/v), from about 0.75% (w/v) to about 2.0% (w/v), from about 0.75% (w/v) to about 1.5% (w/v), from about 0.75% (w/v) to about 1.0% (w/v), from about 1.0% (w/v) to about 2.0% (w/v), or from about 1.0% (w/v) to about 1.5% (w/v).

In certain embodiments, when tested for mucoadhesive properties, for example as described in Example 3, the staining composition including a mucoadhesive agent (either by means of the ASA or a separate mucoadhesive agent) shows a reduction of travel speed along a tilted (for example, tilted at 30° from horizontal) surface containing 2% mucin and 2% agar (simulates gastric tissue lining) by at least 60%, at least 50%, at least 40%, at least 30%, or at least 20% compared to a similar composition lacking the mucoadhesive agent.

IV. Viscosity-Increasing Agents

The composition optionally may also include a viscosity-increasing agent to prevent or otherwise reduce the settling of the carbon particles, and to adjust the viscosity of the composition to a desired level. A viscosity greater than that of water may slow down the settling process but viscosities too high may result in a solution that cannot be injected through a suitable delivery needle, for example, a 25 gauge needle. In certain embodiments, the staining composition is capable of passing through a 25 gauge needle 240 cm in length upon application of a force no greater than about 32N, optionally from about 22 to about 32N, or about 22N or less, or about 10N or less, to push the composition through the needle.

Preferred viscosity-increasing agents include, for example, glycerol, propylene glycol, isopropylene glycol, polyethylene glycol, cellulose, carboxymethyl cellulose, hydroxypropyl methylcellulose, and hyaluronic acid. In certain embodiments the agent is thermally stable and compatible with other formulation components to prevent the carbon particles from rapidly (e.g., less than 60 minutes, 30 minutes, 20 minutes, 10 minutes, or 5 minutes) settling out of solution. In certain embodiments, the viscosity-increasing agent is glycerol. To the extent that the viscosity-increasing agents are not thermally stable, for example, carboxymethyl cellulose and hydroxypropyl methylcellulose, the tissue staining solution may be filter sterilized or other non-thermal approach.

The viscosity-increasing agents can be present in the staining composition at a final concentration of from about 5% to about 25%, 5% to about 20%, 5% to about 15%, 5% to about 10%, 10% to about 25%, 10% to about 20%, 10% to about 15%, 15% to about 25%, or 15% to about 20% (w/v).

V. Additional Additives

The composition may also include other additives, for example, a surfactant, an anti-foaming agent, and/or a preservative.

The compositions optionally comprise a surfactant to reduce or eliminate the reagglomeration of the carbon particles and/or to wet the carbon particles in water-based solvents. The surfactant allows the carbon agglomerates to be more readily dispersed in aqueous solutions and prohibits reagglomeration after sonication/homogenization. In certain embodiments the surfactant is a non-ionic surfactant. In certain embodiments, the surfactant is selected from the group consisting of polyethoxylated sorbitan ester and/or sorbitan ester. Exemplary polyethoxylated sorbitan esters include, for example, PEG-20 sorbitan monolaurate (Tween® 20), PEG-4 sorbitan monolaurate (Tween® 21), PEG-20 sorbitan monopalmitate (Tween® 40), PEG-20 sorbitan monostearate (Tween® 60), PEG-20 sorbitan tristearate (Tween® 65), and PEG-20 sorbitan monooleate (Tween® 80), which are available commercially from Croda Europe Ltd, England. In certain embodiments, PEG-20 sorbitan monooleate (Tween® 80) is preferred. Exemplary sorbitan esters include, for example, Sorbitan monolaurate (Span® 20), Sorbitan monopalmitate (Span® 40), Sorbitan monostearate (Span® 60), Sorbitan monooleate (Span® 80), Sorbitan sesquioleate (Span® 83), Sorbitan trioleate (Span® 85), and Sorbitan isostearate (Span® 120).

In certain embodiments, the surfactant can be present at a final concentration of from about 0.01% to about 4.0% (w/v), from about 0.05% to about 2.0% (w/v), from about 0.05% to about 1.5% (w/v), from about 0.05% to about 1.0% (w/v), from about 0.05% to about 0.75% (w/v), from about 0.5% to about 4% (w/v), from about 0.5% to about 2.0% (w/v), from about 0.5% to about 1.5% (w/v), from about 0.5% to about 1.0% (w/v), from about 0.5% to about 0.75% (w/v), from about 0.75% to about 4% (w/v), from about 0.75% to about 2% (w/v), from about 0.75% to about 1.5% (w/v), or from about 0.75% to about 1.0% (w/v).

Preferred anti-foaming agents include, for example, a dimethicone and simethicone. Simethicone (USP) comprises a mixture of poly(dimethylsiloxane) and silicon dioxide. The poly (dimethylsiloxane) is α-(trimethylsilyl)-ω-methyl-poly[oxy (dimethylsilylene)]. The anti-foaming agent can be present at a final concentration from about 0.01% to about 0.5% (w/v), from about 0.05% to about 0.25% (w/v), or frog about 0.1% to about 0.2% (w/v).

The composition can also include a suitable preservative such as benzyl alcohol, methyl or ethyl paraben, or benzalkonium chloride, which can function as an anti-microbial. In certain embodiments, the preservative is present at a final concentration from about 0.01% to about 4.0% (w/v), from about 0.05% to about 2.0% (w/v), from about 0.05% to about 1.5% (w/v), from about 0.05% to about 1.0% (w/v), from about 0.05% to about 0.75% (w/v), from about 0.5% to about 4% (w/v), from about 0.5% to about 2.0% (w/v), from about 0.5% to about 1.5% (w/v), from about 0.5% to about 1.0% (w/v), or from about 0.5% to about 0.75% (w/v).

Other pharmaceutically acceptable excipients may be added, e.g., buffers such as citrate or phosphate buffering agents. In certain embodiments, the composition does not contain significant amounts of shellac, phenol, polycyclic aromatic hydrocarbons, ammonia, or gelatins.

The pH of the tissue staining composition should be compatible with staining living tissue, and preferably has a pH in the range from about 6 to about 8.

It is understood that each of the foregoing components of the tissue staining solution including, for example, the carbon particles, ASAs, mucoadhesives, viscosity increasing agents, and additional additives are pharmaceutically acceptable. The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

VI. Methods of Manufacture and Use

The tissue staining compositions can be prepared using a variety of approaches.

In a first approach, the marking compositions are produced by making a solution comprising carbon particles having a mean particle diameter less than 0.3 µm, preferably less than 0.2 µm. This can be achieved by, for example, sonicating or homogenizing a carbon particle containing solution, as discussed above. Thereafter, the particles are combined with other excipients, for example, an ASA, a mucoadhesive agent, a surfactant, and other agents etc.

In an exemplary protocol for making a tissue stain containing an ASA, a first pre-mix solution (the carbon pre-mix) is prepared by dissolving a surfactant (e.g., Tween® 80) and an anti-foaming agent (e.g., simethicone) in an aqueous solution (e.g., water), then adding depyrogenated carbon particles and mixing the surfactant, anti-foaming agent and carbon particles to produce a surfactant/carbon particle mixture. The surfactant/carbon particle mixture is then exposed to a deagglomeration procedure (for example, by sonication and/or homogenization) to produce the first pre-mix solution. In this method, the surfactant coats the carbon particles to slow down or prevent agglomeration or reagglomeration of the carbon particles. A second pre-mix solution (the polymer pre-mix) is prepared by combining the ASA (e.g., HEC) with the optional viscosity-increasing agent (e.g., glycerol) by mixing. The glycerol can also wet the ASA (e.g., HEC). The resulting mixture (or the ASA alone) is combined with an aqueous solution (e.g., water). Preferably the ASA (e.g., HEC) is not exposed to the deagglomeration procedure as this may shear the polymer thereby reducing or otherwise eliminating the beneficial properties of the polymer. In other words, the carbon particles are deagglomerated before being mixed with the ASA. A preservative can be added to the first pre-mix solution, the second pre-mix solution or both the first and second pre-mix solutions. The first and second pre-mix solutions then are combined, mixed, and introduced into a suitable container or delivery device, for example, a syringe.

If the final tissue stain lacks the optional ASA and/or viscosity-increasing agent, then the second pre-mix solution can lack the ASA and/or viscosity-increasing agent. An example of a protocol for making a tissue stain without an ASA is described in Example 2. Briefly, a first pre-mix is prepared by combining a surfactant (e.g., Tween® 80), an anti-foaming agent (e.g., simethicone) and a viscosity increasing agent (e.g., glycerol) in water, and then adding the resulting mixture to carbon particles with mixing to produce the first pre-mix. A preservative can be added to the first pre-mix. A second pre-mix is prepared by adding a surfactant (e.g., Tween® 80) to water with stirring. Then a viscosity increasing agent (e.g., glycerol) is added to the mixture to produce the second pre-mix. A preservative can be added to the second pre-mix. Thereafter, the first pre-mix and the second pre-mix are combined with mixing (homogenization) at the appropriate rate and for the appropriate time, for example, for over 20 hours, until a tissue stain containing carbon particles with the desired particle sizes are obtained.

In a second approach, the deagglomerated carbon particles are mixed with the excipients, for example, the optional ASA, mucoadhesive agent, surfactant, etc. and then the carbon particles are filtered with a 0.2 µm filter (or a filter with smaller pore sizes) and size sorted to have a mean particle diameter less than 0.3 µm or less than 0.2 µm.

The resulting tissue staining compositions created by the foregoing approaches and protocols, when introduced in a suitable container, can then be sterilized to maximize shelf life using sterilization techniques known in the art, including, as appropriate, autoclaving, exposure to ionizing radiation or by sterile filtration. Similarly, once the tissue staining composition has been included in a delivery device, the delivery device may be terminally sterilized using one or more procedures known in the art of terminal sterilization, for example, by autoclaving or by exposure to ionizing radiation.

The sterilization process preferably achieves a sterility assurance level (SAL) of $10^{-3}$ or better; i.e. the probability of any given unit of product being non sterile after the process is no more than 1 in $10^3$. More preferably, the sterilization process achieves an SAL of $10^{-4}$ or better, $10^{-5}$ or better, $10^{-6}$ or better, or $10^{-7}$ or better.

The staining composition can be used in the form of a liquid surgical marker for endoscopic and/or laparoscopic marking using known endoscopic and/or laparoscopic techniques. For example, the liquid tissue marking solution can be drawn into a syringe and injected through a needle, for example, a 25 gauge needle into the tissue of interest. In certain embodiments, the composition is capable of passing through a 25 gauge needle 240 cm in length by application of a force no greater than about 32N, for example, from about 22N to about 32N, or about 22N or less, or about 10N or less, or about 7N or less, or about 5N or less, to push the composition through the needle. The choice of the appropriate needle and/or injection system for introducing the tissue stain into the tissue of interest would be apparent to the user.

In certain embodiments, the tissue staining solutions do not include emulsifiers and/or do not contain carbon particles encapsulated in an emulsifier and/or do not contain carbon particles encapsulated in emulsifier containing micelles, as described in U.S. Pat. No. 9,024,087.

An exemplary water based-tissue staining composition suitable for marking gastrointestinal tissue comprises:
(i) from about 0.025% to about 2.0% (w/v) carbon particles having a mean particle diameter less than 0.3 µm or less than 0.2 µm; and
(ii) optionally from about 0.025% to less than 5.0% (w/v) of an ASA selected from hydroxyethyl cellulose (HEC), hydroxypropyl cellulose (HPC), dextran, and guar gum, or a combination thereof (for example, HEC2K or HEC5K or a combination thereof);
(iii) optionally from about 5.0% to about 25% (w/v) of a viscosity-increasing agent (for example, glycerol);
(iv) optionally from about 0.1% to about 2.0% (w/v) of a surfactant (for example, Tween® 80); and
(v) optionally from about 0.005% to about 1.0% (w/v) of an anti-foaming agent (for example, simethicone).

An exemplary water based-tissue staining composition suitable for marking gastrointestinal tissue comprises:
(i) from about 0.025% to about 2.0% (w/v) carbon particles having a mean particle diameter less than 0.3 µm or less than 0.2 µm; and
(ii) optionally from about 0.025% to less than 5.0% (w/v) of an ASA selected from hydroxyethyl cellulose (HEC), hydroxypropyl cellulose (HPC), dextran, and guar gum, or a combination thereof (for example, HEC2K or HEC5K or a combination thereof);

(iii) from about 5.0% to about 25% (w/v) of a viscosity-increasing agent (for example, glycerol);
(iv) from about 0.1% to about 2.0% (w/v) of a surfactant (for example, Tween® 80); and
(v) from about 0.005% to about 1.0% (w/v) of an anti-foaming agent (for example, simethicone).

Another exemplary water-based tissue staining composition suitable for marking gastrointestinal tissue comprises:
(i) 0.025% to 0.5% (w/v) carbon particles having a mean particle diameter less than 0.3 µm or less than 0.2 µm;
(ii) optionally 0.1% to 0.5% (w/v) HEC, for example, HEC2K or HEC5K or a combination thereof;
(iii) optionally about 15% glycerol;
(iv) optionally about 1% Tween® 80;
(v) optionally about 0.01% simethicone; and
(vi) optionally about 1% benzyl alcohol.

Another exemplary water-based tissue staining composition suitable for marking gastrointestinal tissue comprises:
(i) 0.025% to 0.5% (w/v) carbon particles having a mean particle diameter less than 0.3 µm or less than 0.2 µm;
(ii) optionally 0.1% to 0.5% (w/v) HEC, for example, HEC2K or HEC5K or a combination thereof;
(iii) about 15% glycerol;
(iv) about 1% Tween® 80;
(v) about 0.01% simethicone; and
(vi) about 1% benzyl alcohol.

Throughout the description, where apparatus, devices, and systems are described as having, including, or comprising specific components, or where processes and methods are described as having, including, or comprising specific steps, it is contemplated that, additionally, there are apparatus, devices, and systems of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular staining solution, that staining solution can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present invention remains operable. Moreover, two or more steps or actions may be conducted simultaneously.

At various places in the present specification, staining solutions, components, or features thereof are disclosed in groups or in ranges. It is specifically intended that the description include each and every individual subcombination of the members of such groups and ranges. By way of other examples, an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

As a general matter, compositions specifying a percentage are by weight unless otherwise specified.

Practice of the invention will be more fully understood from the foregoing examples, which are presented herein for illustrative purposes only, and should not be construed as limiting the invention in any way.

EXAMPLES

Example 1

Effect of Carbon Particle Size on Darkness of Tissue Stain

This Example shows that carbon particle size has a profound impact on the darkness of a tissue staining composition.

Various test solutions were prepared containing different concentrations of carbon particles ranging from 0.025%-1.0% (w/v) of carbon particles (Monarch 4750 from Cabot Corp., Billerica MA) that were either not deagglomerated and thus contained carbon particles having a mean particle diameter of about 6.6 µm or deagglomerated by sonication to produce carbon particles having a mean diameter less than 0.2 µm. The balance of each test solution included 15% (w/v) glycerol, 1% (w/v) Tween® 80, 1% (w/v) benzyl alcohol, 0.01% (w/v) simethicone, and sterile water for injection (SWFI).

The test solutions were prepared as follows.

A first (2×) pre-mix was prepared by adding the following ingredients to SWFI at 80-100° C., one at a time, and mixing for 15 minutes before adding the next ingredient, to give the following final concentrations of each ingredient in the pre-mix and in the order of addition—15% (w/v) glycerol, then 2% (w/v) Tween® 80, then 2% benzyl alcohol, then 0.02% (w/v) simethicone, then twice the required concentration of the carbon particles desired in the final product when the first pre-mix was mixed with an equal amount of a second pre-mix. The solution was mixed and allowed to cool to room temperature. For the non-sonicated samples, a portion of the resulting solution was stored to be combined with the second pre-mix. For the sonicated samples, a portion of the resulting solution was sonicated using a 350W Biologics Model 3000 Ultrasonic Homogenizer with a solid ½" diameter titanium tip (BioLogics, Inc., Manassas VA) for 3 minutes on 60% power prior to mixing with the second pre-mix.

A second pre-mix was prepared by adding glycerol to SWFI at 80-100° C. to give a final concentration of 15% (w/v) glycerol.

The first and second pre-mixes were then combined by mixing equal amounts of each pre-mix to give the final concentrations of each ingredient, namely, the specified amount of the carbon particles, 15% (w/v) glycerol, 1% (w/v) Tween® 80, 1% (w/v) benzyl alcohol, 0.01% (w/v) simethicone.

The size of the carbon particle size in each final solution was determined using a Nanotrac Wave II Laser Light Scattering Particle Size analyzer without any further dilution or sonication or homogenization.

The darkness of the resulting solutions was measured by densitometry using an x Rite 504 Portable Solar Reflection Spectrodensitometer.

The effect of carbon concentration as well as deagglomeration on the depth color and the resulting % absorbed light is summarized below in TABLE 1, and shown pictorially in FIG. 2.

TABLE 1

| % Carbon Particle Concentration (w/v) | Darkness (% absorbance) - non deagglomerated (mean particle size about 6.6 μm) | Darkness (% absorbance) - deagglomerated (mean particle size less than 0.2 μm) |
| --- | --- | --- |
| 0.025 | Too low to test | 13.5% |
| 0.05 | Too low to test | 31% |
| 0.1 | Too low to test | 42% |
| 0.25 | 18% * | 54% |
| 0.50 | 27% | 60% |
| 1.0 | 43% | 68% |

* The formulation containing 0.25% (w/v) carbon particles is representative of a commercially available carbon-based tissue staining solution containing carbon particles with a mean particle diameter of about 6.6 μm.

Figure 2:
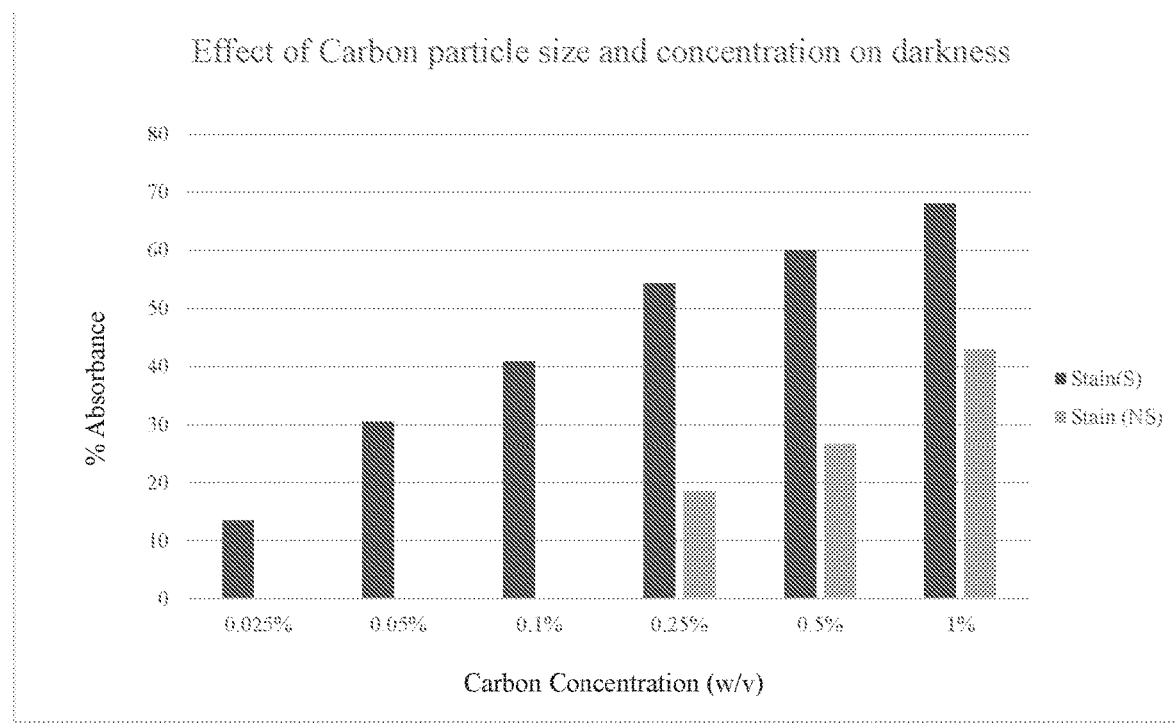
FIG. 2 is a bar chart showing the effect of carbon particle size and concentration on the darkness of tissue staining solution.

As can be seen from TABLE 1 and FIG. 2, higher amounts of carbon particles in a sample can result in darker marking solutions. However, the tissue staining compositions that had a mean particle diameter of less than 0.2 μm were much darker than tissue staining compositions containing a mean particle diameter of about 6.6 μm. This experiment demonstrates that a tissue staining composition containing carbon particles at a concentration of 0.1% (w/v) and having a mean particle diameter less than 0.2 μm is about as dark as a tissue staining composition containing carbon particles having a mean particle diameter of about 6.6 μm at a concentration of 1.0% (w/v), an order of magnitude greater.

A solution containing only 0.025% (w/v) deagglomerated carbon particles has a darkness equivalent to a solution containing 10 times more carbon by weight (0.25% (w/v), that had not been deagglomerated.

Example 2

Effects of Carbon Particle Size on Particle Sedimentation (Settling)

This example demonstrates that the size of the carbon particles can have a profound effect on the settling of the carbon particles.

In this example, two tissue stains were prepared that were the same (containing 1% (w/v) Tween® 80, 15% (w/v) glycerol, 1% (w/v) benzyl alcohol, and 0.01% (w/v) simethicone), and containing 0.27% (w/v) carbon particles (Monarch 4750 from Cabot Corp., Billerica MA) that were either not deagglomerated and thus contained carbon particles having a mean particle diameter of about 6.6 μm or deagglomerated by homogenization to produce carbon particles having a mean diameter less than 0.2 μm. The resulting particles were analyzed for particle size and stability.

The tissue stain containing the deagglomerated carbon particles were prepared from a carbon particle pre-mix containing the ingredients set forth in TABLE 2A, and a Tween® 80 premix set forth in TABLE 2B.

TABLE 2A

Carbon Particle Pre-Mix

| Ingredient | Weight |
| --- | --- |
| Tween ® 80 | 100 mL |
| Glycerin | 210 mL |
| Simethicone | 3.5 mL |
| Benzyl alcohol | 14 mL |
| Carbon (Monarch 4750, Cabot) | 70 g |
| SWFI | 1,072 mL |
| Total: | 1,399.5 mL |

In order to produce the carbon particle pre-mix, the Tween® 80, simethicone and glycerin were added to SWFI at 80° C. Once the ingredients had dissolved, the resulting mixture was cooled to room temperature to produce a Tween® 80, simethicone, glycerin (TSG) mixture. One third of the resulting TSG mixture was combined with all the carbon (Cabot), and the carbon was wetted by stirring slowly until all the all the carbon was wetted. The carbon containing mixture was homogenized for 10 minutes at 4,000 rpm in a mixer (Silverson Model L5M-A) until all the carbon was dispersed in solution without any large clumps. The resulting mixture was then added to another one third of the TSG mixture while the mixer (Silverson Model L5M-A) was running at 1,000 rpm for 5-10 minutes. The remaining one third of the TSG mixture was added to the homogenizing mixture for an additional 45 minutes at 5,600 rpm. The benzyl alcohol was then added for the last 1 minute of homogenization.

The carbon particle pre-mix can be used as is or stored until further processing. If the latter, the carbon particle pre-mix should be homogenized again for 10 minutes at 3,800 rpm (Silverson Model L5M-A) prior to further processing. In this example, the carbon particle containing pre-mix was homogenized for 10 minutes at 3,800 rpm in a (Silverson Model L5M-A) prior to the addition of further reagents, for example, by combination with a Tween® 80 pre-mix, which was prepared containing the ingredients set forth in TABLE 2B.

TABLE 2B

Tween® 80 Pre-mix

| Ingredient | Weight |
| --- | --- |
| Tween80 ® | 162 mL |
| Glycerin | 3,690 mL |
| Simethicone | 0 |
| Benzyl alcohol | 248 mL |
| Cabot Carbon | 0 |
| SWFI | 19,600 mL |
| Premix & Total: | 25,089.5 mL |

The Tween® 80 pre-mix was prepared as follows. 10 L of water was preheated to a temperature in the range of 80° C.-100° C. In a separate container, Tween® 80 was added to about 500 mL of SWFI at 80° C.-100° C. and mixed with stirring for 15 minutes. Then, the benzyl alcohol and glycerin are added to give a mixture, which is then added to the 10 L of water with mixing at 450 rpm. The remaining water was then added to form the Tween® 80 pre-mix.

Thereafter, the carbon-particle pre-mix is then added to the Tween® 80 pre-mix while mixing (ServoDyne Model SSM54) at 700 rpm for 15 minutes and then 450 rpm for 27 hours.

A similar tissue stain containing carbon particles that had not been deagglomerated was produced as follows with the ingredients set forth in TABLE 2C.

TABLE 2C

| Ingredient | Weight |
| --- | --- |
| Tween ® 80 | 262 mL |
| Glycerin | 3,900 mL |
| Simethicone | 3.75 mL |
| Benzyl alcohol | 262 mL |
| Cabot Carbon | 68 g |
| SWFI | 20,745 mL |
| Premix & Total: | 25,172.75 mL |

A Tween® 80 pre-mix was prepared as follows: the Tween80® was added to about 750 mL of SWFI at 80° C.-100° C. and mixed with stirring for 15 minutes. A Simethicone pre-mix was prepared as follows: the simethicone was added to 245 mL of SWFI and mixed for 15 minutes.

The glycerin was added to 10 L of SWFI at 80° C.-100° C. in a ServoDyne mixer operating at 450 rpm and mixed for 10 minutes, and then the remainder of the SWFI was added. Thereafter, the Tween80® pre-mix was added and mixed for 10 minutes, the benzyl alcohol was then added and mixed for 5 minutes, and the simethicone pre-mix was then added and mixed for 5 minutes. Finally the carbon was added, and the resulting mixture mixed for about 20 hours.

Once prepared, the particle sizes of the carbon particles in each tissue stain were measured with a Nanotrac Wave II Laser Light Scattering Particle Size analyzer. The carbon particles in the tissue stain containing the deagglomerated carbon particles had a mean particle size of less than 0.2 µm (0.17 µm), whereas the carbon particles present in the tissue stain that had not been deagglomerated had a mean particle diameter of about 6.6 µm.

In addition, each tissue stain was analyzed with a LUMi-Sizer 650 (LUM BmbH, Berlin, Germany) to determine stability (sedimentation) at room temperature. The sedimentation rates can be expressed as the median sedimentation rate (µm/s) or the D90 sedimentation rate (µm/s; 90% of all the particles have a sedimentation rate less than the D90 value, whereas 10% of the particles have a sedimentation rate higher than the D90 value).

It was found that the tissue stain containing the particles that were not deagglomerated had a median sedimentation rate of about 8 µm/s and a D90 sedimentation rate of about 171 µm/s, whereas the tissue stain containing the particles that were deagglomerated had a median sedimentation rate of 2.7 µm/s and a D90 sedimentation rate of about 4.9 µm/s.

Given the size of the deagglomerated particles in the tissue stain, it is contemplated that sedimentation will be reduced or even eliminated due to Brownian back diffusion if the carbon particles are prevented from reagglomerating, for example, by the presence of an effective amount of a surfactant, for example, a non-ionic surfactant.

Example 3

Carbon Particle-Based Tissue Stains with Desirable Anti-Settling and Mucoadhesive Properties This example demonstrates that it is possible to create a carbon particle-based tissue staining composition that is more resistant to settling than commercially available tissue staining solutions. The size of the carbon particles has a profound effect on the settling of the particles. For example, carbon particles having a mean particle diameter less than 0.3 µm (for example, less than 0.2 µm) exhibit much lower sedimentation over time especially in the presence of an agent, for example, a surfactant, such as a non-ionic surfactant, that prevents reagglomeration of the carbon particles.

However, under certain circumstances, it may be desirable to combine the carbon particles (e.g., in the presence of a surfactant) with an anti-settling agent. This example also demonstrates that the particle size and/or the settling agent can be used to create a tissue staining composition that has the appropriate anti-settling properties.

In addition, if the exemplary tissue staining compositions have mucoadhesive properties, it is contemplated that the carbon particles will not diffuse out of the tissue regions of interest that have been previously marked, thereby permitting users to visualize those regions more clearly and for longer periods of time than when using staining solutions without the mucoadhesive properties.

In this example, various tissue staining compositions were created and analyzed by centrifugation to mimic standing for approximately 7 months. Each composition contained 15% glycerol, 1% Tween® 80, 1% benzyl alcohol and 0.01% simethicone in water. However, each particular tissue staining composition contained either 0.50% (w/v) (TABLE 3) or 0.25% (w/v) (TABLE 4) carbon particles (Monarch 4750 from Cabot Corp., Billerica MA), which were either deagglomerated by sonication as described in Example 1 to reduce particle size or not, together with different types and amounts of polymers (e.g., hydroxyethyl cellulose (HEC, including HEC300, HEC2K, and HEC5K from Spectrum Chemical or Ashland; guar gum (from Spectrum Chemical, Ashland), and hydroxypropyl cellulose (HPC 4956 from Spectrum Chemical, Ashland, or Fisher). Solutions lacking the polymer are referred to as "No polymer—control" in TABLES 3 and 4.

The darkness of the final tissue staining compositions solutions were measured as described in Example 1, and the results expressed as % absorbance.

The settling properties of the carbon particles in each of the various tissue staining compositions were compared by centrifugation. In particular, 5 mL of each sample was placed in a centrifuge tube in a ThermoScientific Multifuge X1R centrifuge and spun at 5,000×g for 60 minutes (representative of settling at about 7 months). This resulted in the settling of a portion of the carbon particles to give a pellet of settled solids at the bottom of each centrifuge tube and a liquid supernatant above the pellet. An aliquot from the one third of the supernatant was then removed and analyzed by UV/visible spectrometry to determine carbon concentration, which was then compared to the carbon concentration in the sample prior to centrifugation. Samples with less settling have more carbon remaining in the top third of the liquid after centrifugation, resulting in a lower percent loss.

The mucoadhesive properties of the tissue staining compositions were also assayed. Briefly, an agar plate comprising 2% porcine mucin and 2% agar was prepared by dissolving 20 grams of granulated agar and 20 grams of porcine mucin in 1000 mL of distilled water by boiling for 20 minutes. The molten mucin-agar mix was poured into a plastic container with dimensions of approximately 13 inches long, 10 inches wide, and 2 inches deep. The mucin-agar mix was allowed to solidify at room temperature. Then 75 μL of each sample was applied as spots to the surface of the test plate, then the plates were inclined at an angle of 30 degrees relative to horizontal and the distance travelled down the plate was measured after one minute. Samples that traveled a shorter distance are more mucoadhesive than samples that traveled a longer distance.

The results are summarized in TABLES 3 and 4.

Figure 3:
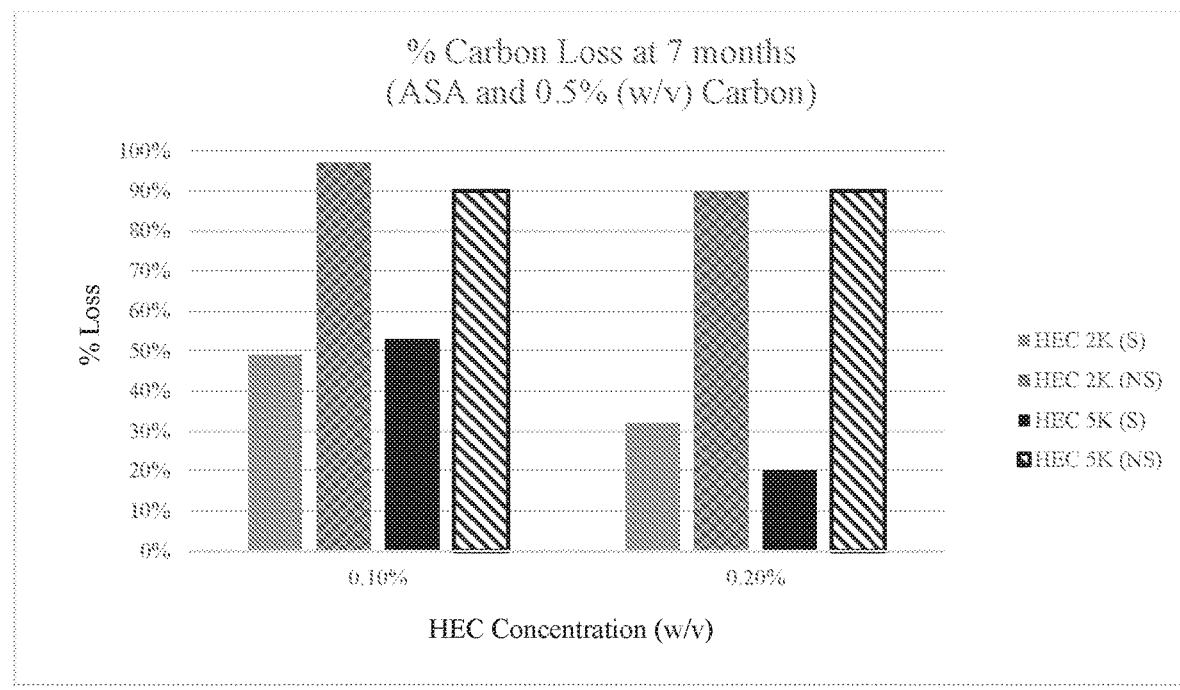
FIG. 3 is a bar chart showing that the anti-settling properties of a carbon particle-based tissue staining solution containing 0.50% (w/v) carbon particles is based upon the combination of particle size and the presence of a sufficient amount of an ASA.

The results are also compiled as a bar chart in FIG. 3. The results demonstrate (e.g., by comparing the results from samples 7, 10 and 11) that, in order to prevent settling of the particles over prolonged periods of time, it is necessary to reduce the size of the carbon particles (compare samples 10 and 11) and to include an appropriate amount of a polymer that demonstrates anti-settling properties (compare samples 7 and 10). In particular, when the particles were deagglomerated by sonication and present in a solution containing 0.2% HEC5K (sample 10), less than 20% of the particles settled out under the conditions tested. However, when only 0.05% HEC5K (sample 7) was present in the sample, over 80% of the particles settled under the conditions tested, and when the particles were not deagglomerated but yet present in a solution containing 0.20% HEC5K (sample 10) approximately 90% of the particles settled out under the conditions tested. Similar trends where observed when HEC2K was used instead of HEC5K.

With regard to mucoadhesion, it was found that the HEC2K and HEC5K, in addition to preventing the settling of the particles, also were mucoadhesive. When the staining solution lacked a polymer, the solution migrated along the mucin/agar plates about 20 cm in 1 minute, whereas the staining solution containing 0.20% HEC5K migrated about 8.8 cm in a minute.

All of the solutions (Sample Nos. 1-16) required less than 23N of applied pressure to pass the solution through a 25 gauge needle having a length of 240 cm (Interject, Boston Scientific, MA). As a result, it is contemplated these test solutions can be delivered by such an injection needle to facilitate marking of gastrointestinal tissue.

TABLE 3

0.50% (w/v) Carbon Particles

| Sample No. | % Polymer (w/v) | Deagglomerated particles (Y/N) | Darkness (% abs) | Settling (% loss upon centrifugation) | Mucoadhesion (travel (cm)) |
|---|---|---|---|---|---|
| 1 | 0.2% HEC 300 | Y | 71% | 74% | 13.8 |
| 2 | 0.10% HEC 2K | Y | 68% | 49% | 13.5 |
| 3 | 0.10% HEC 2K | N | 22% | 97% | 13 |
| 4 | 0.15% HEC 2K | Y | 68% | 31% | 11 |
| 5 | 0.20% HEC 2K | Y | 61% | 32% | 10.3 |
| 6 | 0.20% HEC 2K | N | 26% | 90% | 9.0 |
| 7 | 0.05% HEC 5K | Y | 70% | 83% | 17.5 |
| 8 | 0.10% HEC 5K | Y | 69% | 53% | 14 |
| 9 | 0.10% HEC 5K | N | 37% | 90% | 13 |
| 10 | 0.20% HEC 5K | Y | 61% | 20% | 8.8 |
| 11 | 0.20% HEC 5K | N | 21% | 90% | 7.5 |
| 12 | 0.15% Guar gum | Y | 67% | 56% | 12.3 |
| 13 | 0.30% Guar gum | Y | 61% | 58% | 5 |
| 14 | 0.1% HPC 4956 | Y | 64.9% | 80% | 16.25 |
| 15 | No polymer - control | Y | 60% | 85% | 20 |
| 16 | No polymer - control | N | 27% | 98% | 19.5 |

TABLE 4

0.25% (w/v) Carbon Particles

| Sample No. | % Polymer (w/v) | Deagglomerated carbon particles (Y/N) | Darkness (% abs) | Settling (% loss upon centrifugation) | Mucoadhesion (travel (cm)) |
|---|---|---|---|---|---|
| 17 | 0.10% HEC 2K | Y | 46% | 81% | 13 |
| 18 | 0.10% HEC 2K | N | 18% | 92% | 13 |
| 19 | 0.20% HEC 2K | Y | 49% | 11% | 9 |
| 20 | 0.20% HEC 2K | N | 20% | 86% | 9 |
| 21 | 0.10% HEC 5K | Y | 60% | 35% | 12.5 |
| 22 | 0.10% HEC 5K | N | 22% | 92% | 12.5 |
| 23 | 0.20% HEC 5K | Y | 47% | 13% | 7.5 |
| 24 | 0.20% HEC 5K | N | 16% | 86% | 7.5 |
| 25 | No polymer - control | Y | 54% | 92% | 20 |
| 26* | No polymer - control | N | 18% | 98% | 19.8 |

*This formulation is representative of a commercially available carbon particle-based tissue staining solution.

Figure 4:
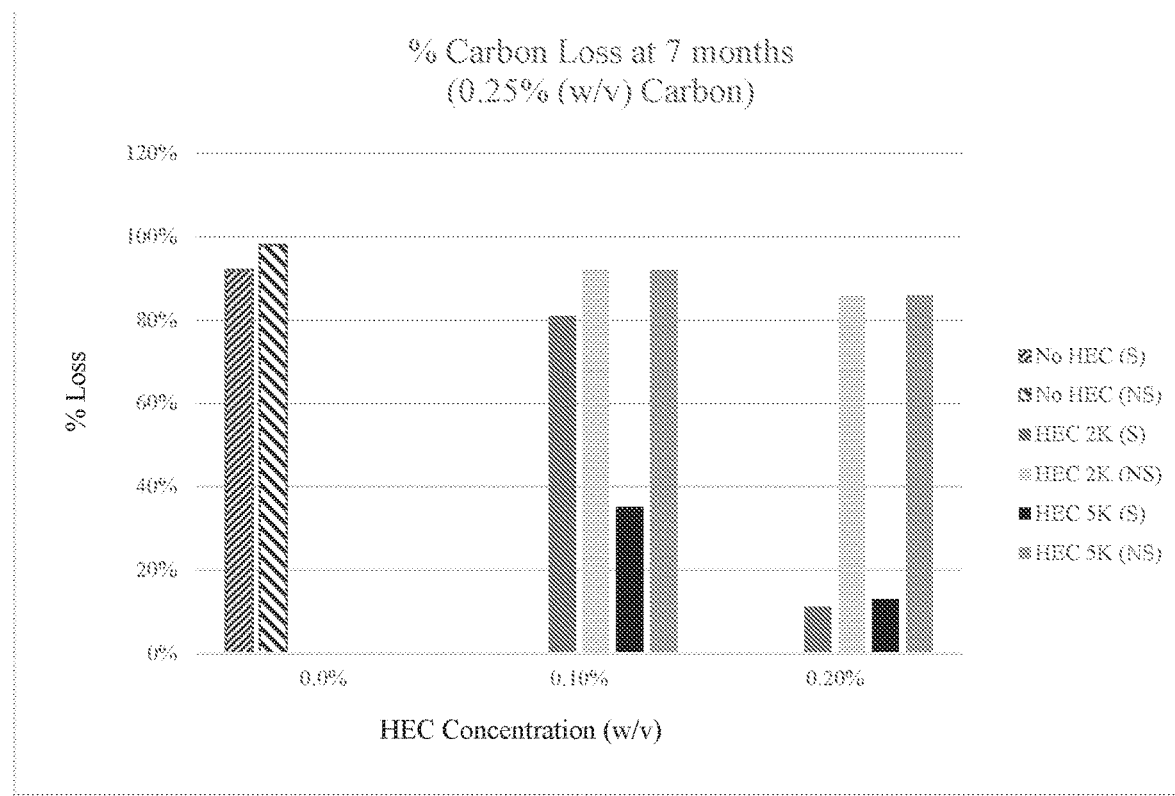
FIG. 4 is a bar chart showing that the anti-settling properties of a carbon particle-based tissue staining solution containing 0.25% (w/v) carbon particles is based upon the combination of particle size and the presence of a sufficient amount of an ASA.
Figure 5:
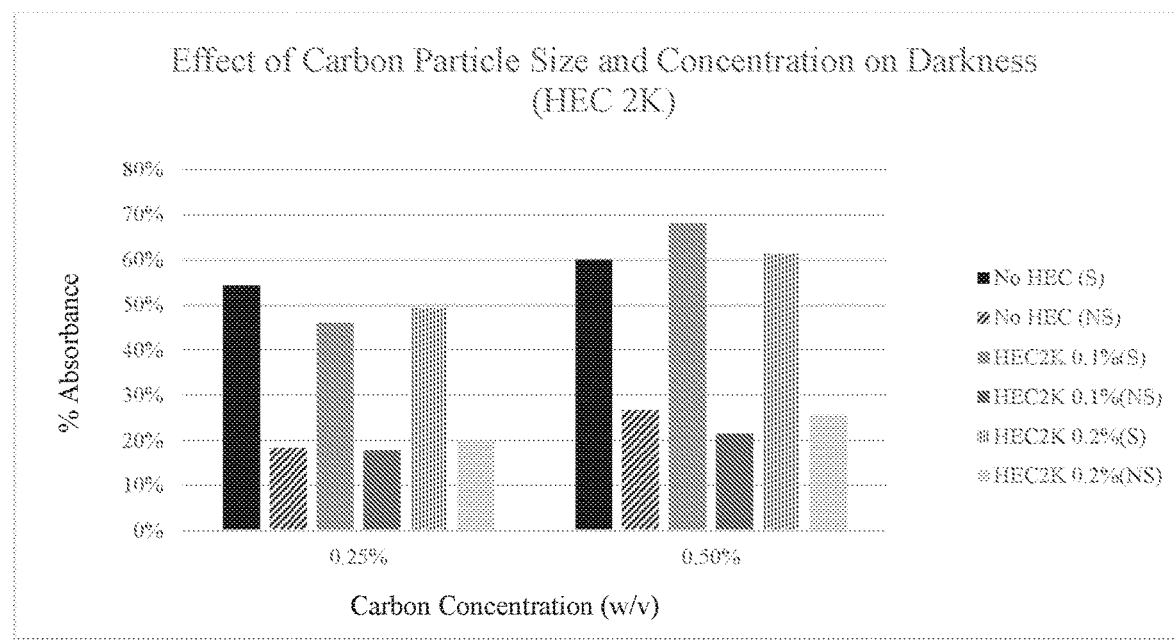
FIG. 5 is a bar chart showing the effect of carbon particle size and concentration on the darkness of tissue staining solutions containing the ASA, HEC 2K.

The results from TABLE 4 are also compiled as a bar chart in FIG. 4.

Similar results were obtained when the carbon particle concentration was lowered from 0.5% to 0.25% (w/v). For example, by comparing the results from samples 19 and 20 (both containing 0.2% HEC2K), when the carbon particles were deagglomerated by sonication, only about 11% of the particles settled out (sample 19) under the conditions tested, but when the carbon particles were not deagglomerated, about 90% of the particles settled out (sample 20) under the conditions tested. Similar results were observed when HEC2K was replaced with HEC5K (see samples 23 and 24).

Figure 6:
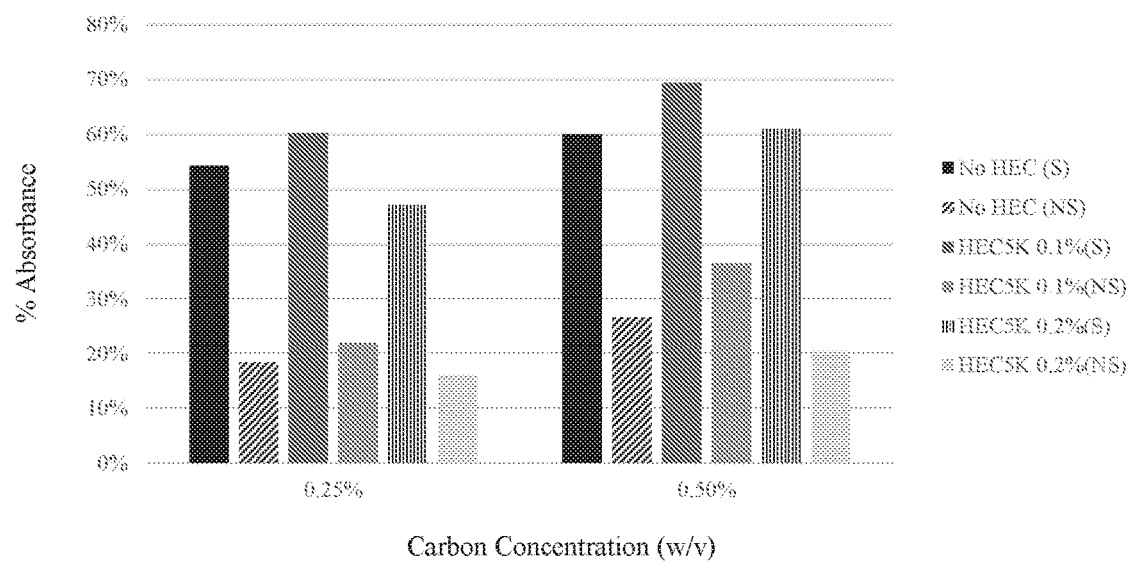
FIG. 6 is a bar chart showing the effect of carbon particle size and concentration on the darkness of tissue staining solutions containing the ASA, HEC 5K.

The darkness of each of the solutions set forth in TABLES 3 and 4 were tested as described in Example 1. The results are summarized in FIGS. 5 and 6. The results demonstrate that the effect of particle size in the presence of an anti-settling agent (for example, HEC2K or HEC5K) can have a profound impact on the darkness of the carbon particles. See FIGS. 5 and 6, which represent the darkness of solutions containing 0.25% or 0.5% (w/v) carbon particles that had been sonicated (S) or not sonicated (NS) in the presence of HEC2K (FIG. 5) or HEC5K (FIG. 6). The results demonstrate that sonication (deagglomeration) of the carbon particles has a profound effect on the darkness (expressed as % absorbance) of the staining solutions. Even in the presence of ASA, the solutions containing carbon particles having a mean particle diameter less than 0.3 µm were much darker than comparable solutions where the carbon particles were not deagglomerated by sonication and had a mean particle diameter of about 6.6 µm.

With regard to mucoadhesion, it was found that the HEC2K and HEC5K, in addition to preventing the settling of the particles, also were mucoadhesive. When the staining solution lacked a polymer (see, samples 25 and 26), the solution migrated on the mucin/agar plates about 20 cm in 1 minute, whereas the staining solution containing 0.20% HEC5K migrated only about 8 cm in a minute.

Figure 7:
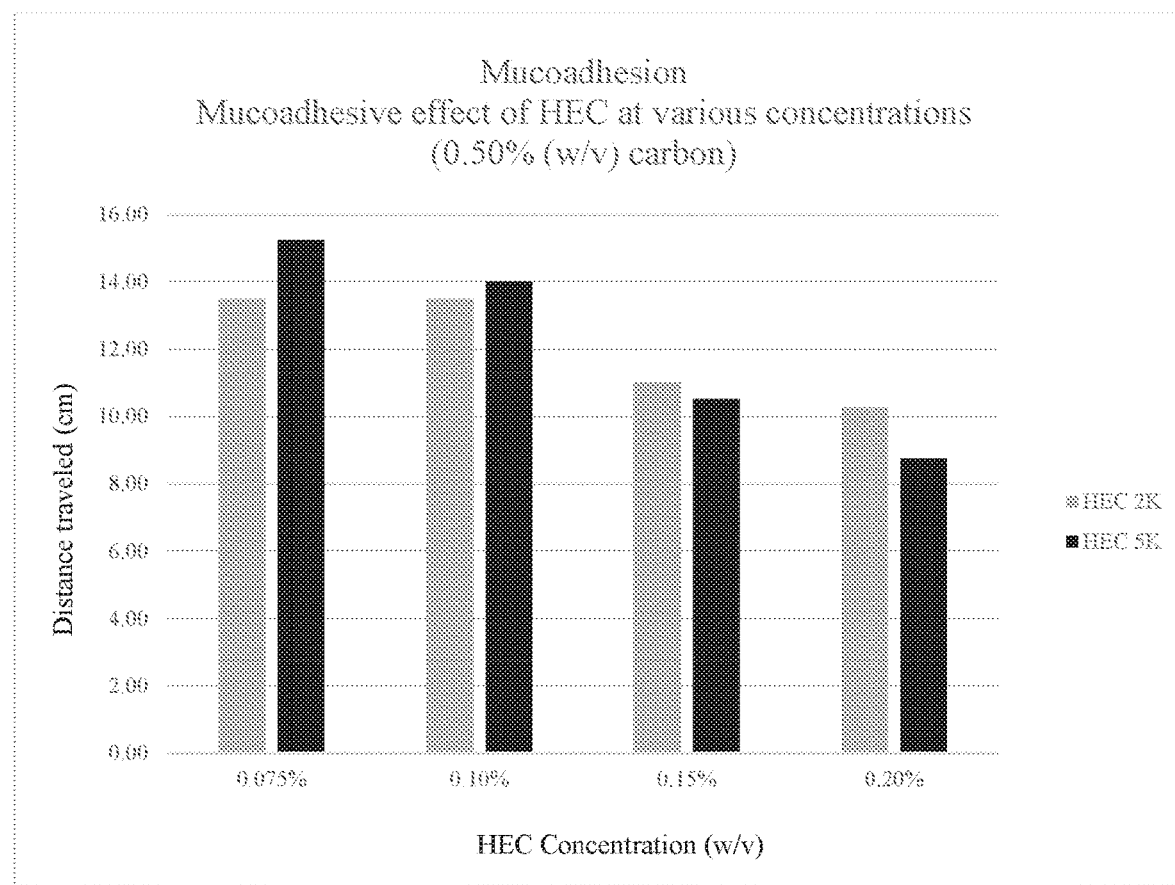
FIG. 7 is a bar chart showing the mucoadhesive properties of exemplary carbon particle-based tissue staining solutions based upon migration speed along a tilted mucin/agar gel.

The results are also shown in FIG. 7, which demonstrates that as the concentration of the ASA with mucoadhesive properties (e.g., HEC2K or HEC5K) increased (for example, from 0.075% to 0.2% (w/v)), the mucoadhesive properties of the tissue staining solution also increased, as expressed by the distance travelled over 1 minute. The higher the concentration of the HEC, the shorter the distance travelled on the agar/mucin plates. These results are shown visually in FIG. 8, which show that HEC5K has mucoadhesive properties, and that the tissue staining compositions visually look much darker to the eye when the size of the carbon particle agglomerates have been reduced by sonication. Staining solutions containing guar gum also were mucoadhesive.

Figure 8A:
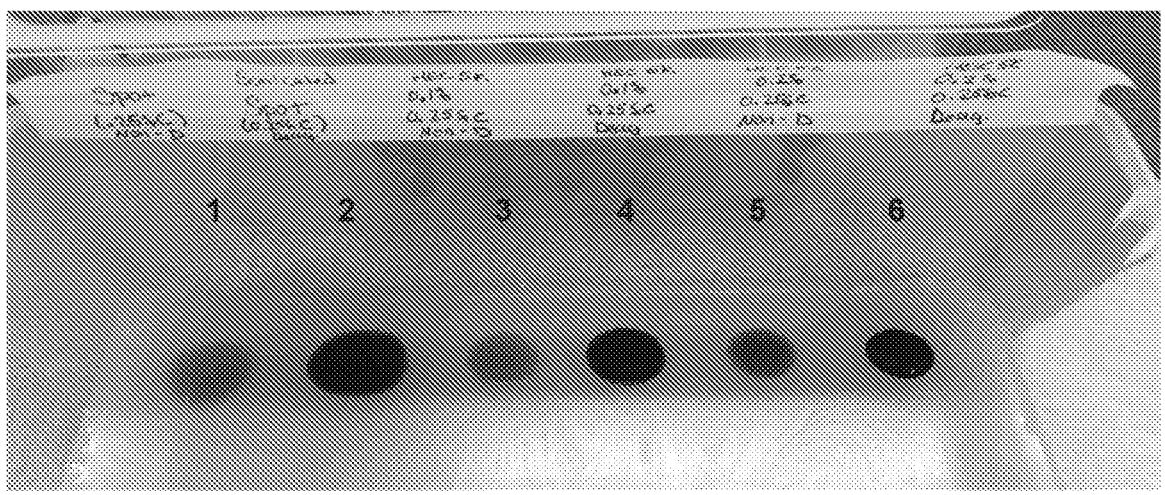
FIGS. 8A and 8B are pictures visually showing the darkness and mucoadhesive properties of various staining solutions containing either HEC 5K before the agar/mucin plate was tilted (FIG. 8A) or after the plate was tilted (FIG. 8B).
Figure 8B:
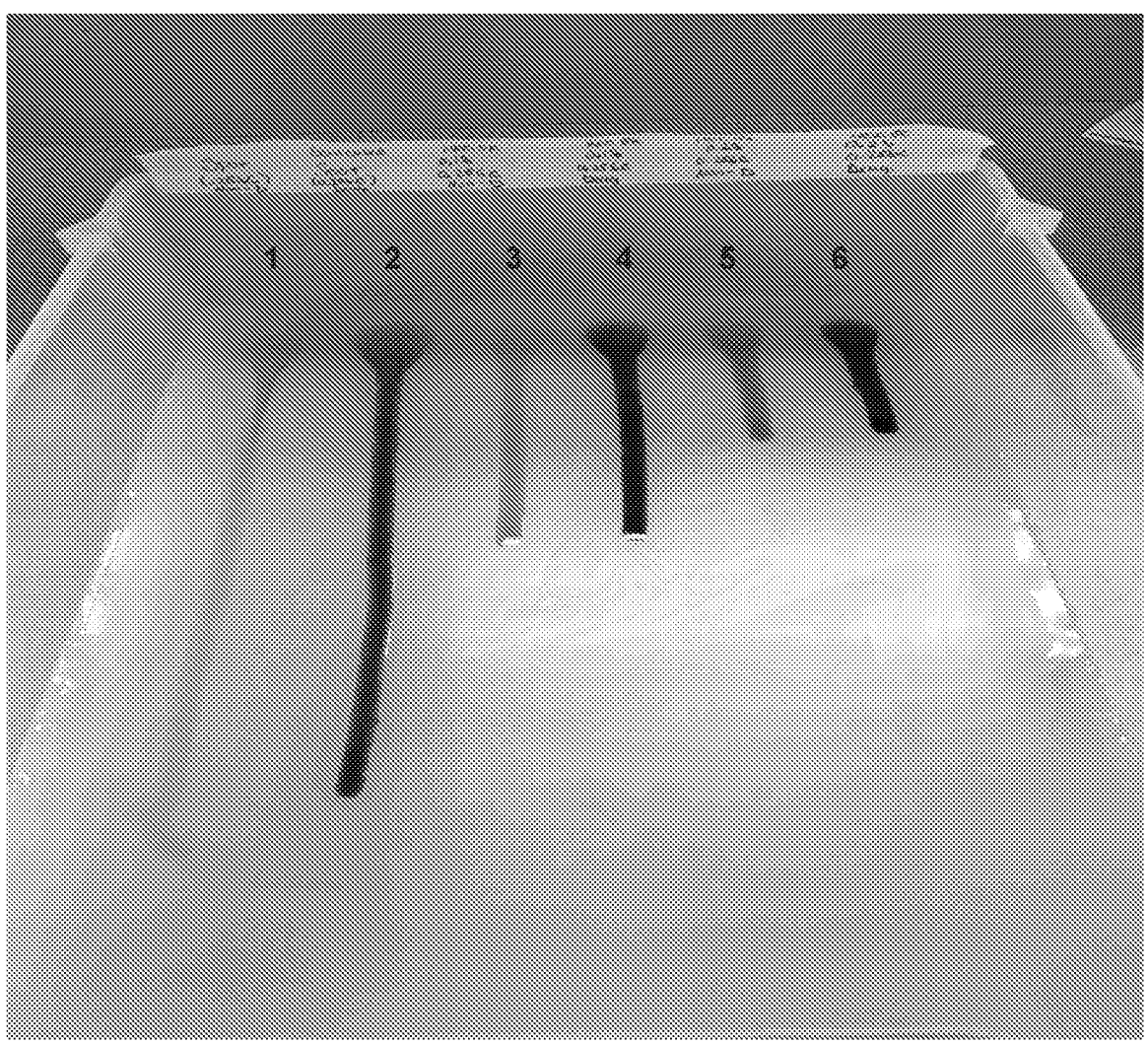

The darkness and mucoadhesive properties are shown visually in FIGS. 8A and 8B where the stains containing different concentrations of HEC5K in the presence of 0.25% (w/v) carbon particles which are not deagglomerated. In each of FIGS. 8A and 8B, samples 1, 2, 3, 4, 5, and 6 correspond to respective staining solutions 26 (no HEC, non-deagglomerated carbon particles), 25 (no HEC, deagglomerated carbon particles), 22 (0.1% HEC5K, non-deagglomerated carbon particles), 21 (0.1% HEC5K, deagglomerated carbon particles), 24 (0.2% HEC5K, non-deagglomerated carbon particles), and 23 (0.2% HEC5K, deagglomerated carbon particles). The staining solutions containing the deagglomerated carbon particles (lines 2, 4, 6) were much darker than the staining solutions containing the non-deagglomerated carbon particles. Furthermore, as the concentration of HEC increased, the samples were more mucoadhesive as demonstrated by the size of each spot before the plates were tilted (FIG. 8A) where the smaller spots were more mucoadhesive, and after the plates were tilted (FIG. 8B) where the samples that travelled the shortest distance were the most mucoadhesive.

The exemplary stains described in this Example are much more mucoadhesive than comparable, surfactant containing, commercially available carbon particle-based tissue stains. As a result, it is contemplated that the tissue stains of the invention will not diffuse or bleed out of the tissue regions of interest that have been previously marked, thereby permitting users to visualize those regions more clearly and for longer periods of time than when using the prior art stain.

All of the solutions (Sample Nos. 17-26) required less than 23N of applied pressure to press the solution through a 25 gauge needle having a length of 240 cm (Injector, Boston Scientific, MA). As a result, each of the tissue stains in this example can be introduced into a tissue of interest using commercially available needles and/or injection systems.

INCORPORATION BY REFERENCE

The entire disclosure of each of the patent and scientific documents referred to herein is incorporated by reference for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A liquid tissue staining composition comprising:
   deagglomerated carbon particles at a concentration of from about 0.025% to 2.0% (w/v) having a mean particle diameter of from about 0.05 μm to less than 0.2 μm;
   an anti-settling agent; (ASA) at a concentration of from about 0.1% to about 1.0% (w/v), and wherein the ASA is selected from the group of hydroxyethyl cellulose, hydroxypropyl cellulose, dextran, and guar gum; and
   an optional mucoadhesive agent.

2. The composition of claim 1, wherein, when centrifuged for 60 minutes at 5,000×g, less than 50% of the carbon particles settle out of solution.

3. The composition of claim 1, wherein the ASA is also a mucoadhesive agent.

4. The composition of claim 1, wherein the mucoadhesive agent is present in the composition.

5. The composition of claim 4, wherein the mucoadhesive agent is hydroxyethyl cellulose, hydroxypropyl cellulose, dextran, or guar gum.

6. The composition of claim 1, further comprising a viscosity-increasing agent.

7. The composition of claim 6, wherein the viscosity-increasing agent is present at a concentration of from about 5% to about 25% (w/v).

8. The composition of claim 6, wherein the viscosity-increasing agent is selected from the group consisting of glycerol, propylene glycol, isopropylene glycol, polyethylene glycol, and cellulose.

9. The composition of claim 1, further comprising an anti-foaming agent.

10. The composition of claim 9, wherein the anti-foaming agent is present at a concentration of from about 0.005% to about 1.0% (w/v).

11. The composition of claim 9, wherein the anti-foaming agent is selected from the group consisting of dimethicone and simethicone.

12. The composition of claim 1, further comprising a surfactant.

13. The composition of claim 12, wherein the surfactant is a non-ionic surfactant.

14. The composition of claim 12, wherein the surfactant is present at a concentration of from about 0.01% to about 2.0% (w/V).

15. The composition of claim 12, wherein the surfactant is selected from the group consisting of polyoxyethylene sorbitan esterified with fatty acid.

16. The composition of claim 1, wherein the carbon particles are derived from carbon black, activated carbon, unactivated carbon or a combination thereof.

17. The composition of claim 1, wherein the carbon particles have a level of polycyclic aromatic hydrocarbons of no greater than 0.5 ppm based on the total amount of carbon particles.

18. The composition of claim 1, wherein the composition is terminally sterilized.

19. The composition of claim 1, comprising:
   (a) from about 0.025% to 2.0% (w/v) carbon particles; from 0.1% to about 1% (w/v) of the ASA selected from the group consisting of hydroxyethyl cellulose, hydroxypropyl cellulose, dextran, and guar gum; when present from about 5.0% to about 25% (w/v) viscosity-increasing agent; from about 0.005% to about 1.0% (w/v) anti-foaming agent; from about 0.1% to about 2.0% (w/v) surfactant; and water; or
   (b) from about 0.025% to about 1.0% (w/v) carbon particles; from about 0.25% to about 1.0% (w/v) of the ASA; from about 12% to about 18% (w/v) of viscosity-increasing agent; from about 0.05% to about 0.25% (w/v) anti-foaming agent; and from about 0.7% to about 1.5% (w/v) surfactant; and water.

20. The composition of claim 1 further comprising a preservative, optionally benzyl alcohol.

21. A method of preparing the tissue staining composition of claim 1, the method comprising:
   (a) producing a composition comprising deagglomerated carbon particles having a mean particle diameter of less than 0.2 μm in diameter and optionally a surfactant; and optionally
   (b) combining the composition comprising the carbon particles with an optional ASA and an optional mucoadhesive agent to produce the tissue staining composition.

22. The method of claim 21, wherein the carbon particles in step (a) are produced by sonicating or homogenizing carbon particles having mean particle diameter of greater than 5 μm in diameter.

23. The method of claim 21, wherein, during step (a), the composition comprises the surfactant and further comprises an anti-foaming agent.

24. A method of staining a region of tissue in a subject, the method comprising injecting the tissue staining composition of claim 1 into the region of tissue of interest in the subject in an amount effective to stain the region so as to be visible by visual inspection.

25. The method of claim 24, wherein the tissue is tissue present in the gastrointestinal tract, bladder, lung, breast, lymph node, or central or peripheral nervous system of the subject.

* * * * *

UNITED STATES PATENT AND TRADEMARK OFFICE
CERTIFICATE OF CORRECTION

| | | |
|---|---|---|
| PATENT NO. | : 12,285,499 B2 | Page 1 of 1 |
| APPLICATION NO. | : 17/942390 | |
| DATED | : April 29, 2025 | |
| INVENTOR(S) | : Mary Jo Timm et al. | |

It is certified that error appears in the above-identified patent and that said Letters Patent is hereby corrected as shown below:

In the Claims

At Column 27, Line 14, "agent; (ASA)" should be -- agent (ASA) --.

At Column 27, Line 52, "(w/V)." should be -- (w/v). --.

At Column 28, Line 24, "and from" should be -- from --.

Signed and Sealed this
Sixteenth Day of September, 2025

Coke Morgan Stewart
*Acting Director of the United States Patent and Trademark Office*